United States Patent
Cook et al.

(10) Patent No.: US 6,472,431 B2
(45) Date of Patent: Oct. 29, 2002

(54) MICROBIOLOGICALLY SOUND AND STABLE SOLUTIONS OF GAMMA-HYDROXYBUTYRATE SALT FOR THE TREATMENT OF NARCOLEPSY

(75) Inventors: Harry Cook, Eden Prairie; Martha Hamilton, St. Paul, both of MN (US); Douglas Danielson, Otsego, MI (US); Colette Goderstad, St. Paul; Dayton Reardan, Excelsior, both of MN (US)

(73) Assignee: Orphan Medical, Inc., Minnetonka, MN (US)

( * ) Notice: Subject to any disclaimer, the term of this patent is extended or adjusted under 35 U.S.C. 154(b) by 0 days.

(21) Appl. No.: 09/470,570

(22) Filed: Dec. 22, 1999

(65) Prior Publication Data

US 2002/0077334 A1 Jun. 20, 2002

Related U.S. Application Data

(60) Provisional application No. 60/113,745, filed on Dec. 23, 1998.

(51) Int. Cl.[7] ............... A61K 31/19; A61K 31/235; A61K 31/34; A61K 31/215
(52) U.S. Cl. ............... 514/557; 514/473; 514/533; 514/529
(58) Field of Search ............... 514/533, 923, 514/937, 944, 529, 557, 811, 812; 424/451, 464

(56) References Cited

U.S. PATENT DOCUMENTS

| 4,983,632 A | * | 1/1991 | Gessa et al. | 514/557 |
| 5,380,937 A | | 1/1995 | Koehler et al. | 562/579 |
| 5,840,331 A | * | 11/1998 | Van Cauter et al. | 424/464 |
| 5,990,162 A | * | 11/1999 | Scharf | 514/533 |

FOREIGN PATENT DOCUMENTS

| EP | 0344704 | 5/1989 | 61/31 |
| EP | 0616804 | 3/1994 | 61/31 |
| EP | 0635265 | 7/1994 | 61/31 |
| GB | 922029 | 3/1963 | 61/81 |
| WO | 40105 | 12/1996 | 61/31 |

* cited by examiner

Primary Examiner—Zohreh Fay
Assistant Examiner—Brian-Yong S. Kwon
(74) Attorney, Agent, or Firm—Schwegman, Lundberg, Woessner & Kluth, P.A.

(57) ABSTRACT

Disclosed are formulations of gamma-hydroxybutyrate in an aqueous medium that are resistant to microbial growth. Also disclosed are formulations of gamma-hydroxybutyrate that are also resistant to the conversion into GBL. Disclosed are methods to treat sleep disorders, including narcolepsy, with these stable formulations of GHB. The present invention also provides methods to treat alcohol and opiate withdrawal, reduced levels of growth hormone, increased intracranial pressure, and physical pain in a patient.

7 Claims, 1 Drawing Sheet

Figure 1.

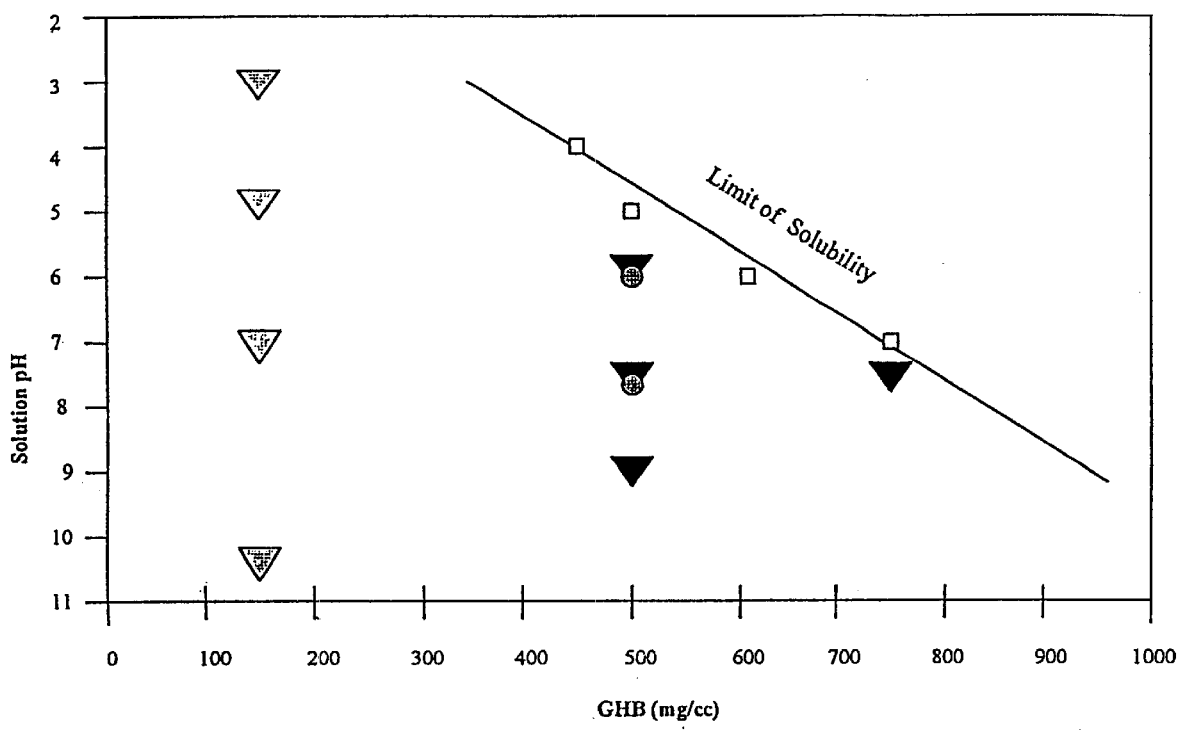

☐ Data points indicating limit of solubility of GHB as a function of concentration and pH, see Table 1.

▽ Solutions susceptible to microbial growth, designated "Fail".
(All solutions demonstrated activity against Pseudomonas aeruginosa. Some reduction of aspergillus niger mold occurred in 7 days of contact time.)

▼ Solutions resistant to microbial growth, designated "Pass". (Rate of reduction of microorganism counts was slightly higher at pH 7.5 and 6.0 than pH 9.0. The rate of reduction of formulations at 750mg/cc GHB were slightly lower than formulations at 500 mg/cc GHB.)

⊕ Solutions rresistant to microbial growth, designated "Pass". Results were similar for Malic Acid and HCl. Taste variations has implications for development of flavor systems.

▽ ▼ Indicates pH adjustment with HCl.
⊕ Indicates pH adjustment with Malic Acid.

Note: Solutions with pH at 9.0 are not palatable or safe for oral consumption.

US 6,472,431 B2

MICROBIOLOGICALLY SOUND AND STABLE SOLUTIONS OF GAMMA-HYDROXYBUTYRATE SALT FOR THE TREATMENT OF NARCOLEPSY

RELATED APPLICATIONS

This application claims priority from Provisional Application No. 60/113,745 filed Dec. 23, 1998, which is incorporated by reference herein.

BACKGROUND OF THE INVENTION

I. Field of the Invention

The present invention relates generally to the fields of pharmaceutical compositions to be used in treatments, such as, sleeping disorders, such as, e.g., narcolepsy (particularly cataplexy), drug abuse, alcohol and opiate withdrawal, a reduced level of growth hormone, anxiety, analgesia, effects in certain neurological disorders such as Parkinson's Disease, depression, certain endocrine disturbances and tissue protection following hypoxia/anoxia such as in stroke or myocardial infarction, or for an increased level of intracranial pressure or the like. The present invention particularly relates to the field of pharmaceutical production of microbiologically resistant and chemically stable preparations or solutions of gamma-hydroxybutyrate (GHB), also known as 4-hydroxybutyrate, and the sodium salt of GHB (sodium oxybate) and other salts such as magnesium, ammonium and calcium, e.g.

II. Description of Related Art

GHB is an endogenous compound with hypnotic properties that is found in many human body tissues. GHB is present, for example, in the mammalian brain and other tissues. In brain the highest GHB concentration is found in the hypothalamus and basal ganglia and GHB is postulated to function as a neurotransmitter (Snead and Morley, 1981). The neuropharmacologic effects of GHB include increases in brain acetylcholine, increases in brain dopamine, inhibition of GABA-ketoglutarate transaminase and depression of glucose utilization but not oxygen consumption in the brain. GHB is converted to succinate and then metabolized via the Krebs cycle. Clinical trials have shown that GHB increases delta sleep and improves the continuity of sleep (Ladinsky et al., 1983; Anden and Stock, 1973; Stock et al., 1973; Laborit, 1973; Lapierre et al., 1988; Lapierre et al., 1990; Yamda et al., 1967; Grove-White and Kelman, 1971; Scharf, 1985).

GHB has typically been administered in clinical trials as an oral solution (Lee, 1977; Mamelak, 1977; Hoes, 1980; Scharf, 1985; Scrima, 1990; Gallimberti, 1992; Series, 1992; Lammers, 1993). GHB treatment substantially reduces the signs and symptoms of narcolepsy, i.e. daytime sleepiness, cataplexy, sleep paralysis and hypnagogic hallucinations. In addition, GHB increases total sleep time and REM sleep, and it decreases REM latency (Mamelak et al, 1973; Yamada et al., 1967; Bedard et al., 1989), reduces sleep apnea (Series et al, 1992; Scrima et al., 1987), and improves general anesthesia (Hasenbos and Gielen, 1985).

GHB has several clinical applications other than narcolepsy and sleep disorders. GHB has been reported to reduce alcohol craving, the number of daily drinks consumed, and the symptoms of alcohol withdrawal in patients (Gallimberti et al., 1989; Gallimberti et al., 1992; Gessa et al., 1992). GHB has been used to decrease the symptoms of opiate withdrawal. including both heroin and methadone withdrawal (Gallimberti et al, 1994; Gallimberti et al., 1993). It has analgesic effects that make it suitable as a pain reliever (U.S. Pat. No. 4,393,236). Intravenous administration of GHB has been reported to reduce intracranial pressure in patients (Strong, A. 1984). Also, administration of GHB was reported to increase growth hormone levels in patients (Gerra et al, 1994; Oyama et al., 1970).

A good safety profile for GHB consumption, when used long term for treatment of narcolepsy, has been reported. Patients have been safely treated for many years with GHB without development of tolerance (Scharf, 1985). Clinical laboratory tests carried out periodically on many patients have not indicated organ or other toxicities (Lammers, 1993; Scrima, 1990; Scharf, 1985; Mamelack, 1977; Mamelak, 1979; Gallimberti, 1989; Gallimberti, 1992; Gessa, 1992). The side effects of GHB treatment have been minimal in incidence and degree of severity, though they include sleepwalking, enuresis, headache, nausea and dizziness (Broughton and Mamelak, 1979; Mamelak et al., 1981; Mamelak et al., 1977; Scrima et al., 1989; Scrima et al., 1990; Scharf et al., 1985).

The pharmacokinetics of GHB have been investigated in alcohol dependent patients (Ferrara et al., 1992) and in normal healthy males (Palatini et al., 1993) after oral administration. GHB possesses a rapid onset and short pharmacological effect (Ferrara et al., 1992; Palatine et al., 1993; Lee, C., 1977; van der Bogert; Gallimberti, 1989; Gallimberti, 1992; Lettieri and Fung, 1978; Arena and Fung, 1980; Roth and Giarman, 1966; Vickers, 1969; Lee, 1977). In alcohol dependent patients, GHB absorption into and elimination from the systemic circulation were fast processes. Virtually no unchanged drug could be recovered in the urine. There were preliminary indications that the pharmacokinetics of GHB might be non-linear or dose-dependent (Ferrara et al., 1992). In the healthy volunteers study, the pharmacokinetics of three rising GHB doses (12.5, 25, and 50 mg/kg) were investigated. These findings indicate that both the oral absorption and elimination processes of GHB were capacity-limited though the degree of dose dependency was moderate (Palatini et al., 1993).

Organic salts and amides of GHB have been produced to reduce the physiological side effects of GHB (U.S. Pat. No. 5,380,937). Magnesium and calcium salt have been produced to reduce the hygroscopic nature of GHB or powdered forms (U.S. Pat. No. 4,393,236; British Patent No. 922,029). However, problems with the storage of GHB solutions still exist. GHB degrades into gamma-butyrolactone (GBL) and possibly other degradants in solution depending upon the pH and other factors. Also, the contamination by microorganisms in GHB solutions rapidly surpass acceptable limits, and preservatives can adversely affect the pH and thus, GHB's stability. As a chronically used product which requires high levels of drug, the volume of a non-concentrated product creates cost and handling issues. Thus, there is an immediate need for effective solutions of GHB that are stable to biological or chemical degradation.

SUMMARY OF THE INVENTION

The present invention overcomes deficiencies in the prior art by providing compositions of GHB in an aqueous medium that are resistant to microbial growth. These compositions are also resistant to the uncontrolled degradation of GHB into GBL or other substances. The compositions of the present invention are stable compositions of GHB that improve shelf-life, and provide a titratable formulation of GHB for easy dose measurement. In addition, the concentrated solutions embodied in this invention reduce shipping and storage requirements and allow patients to carry more drugs for their convenience. The present invention provides methods to treat a number of conditions treatable by GHB, referred to herein as "therapeutic categories." Therapeutic categories for the present invention include, but are not limited to, sleeping disorders, drug abuse, alcohol and opiate withdrawal, a reduced level of growth hormone, anxiety, analgesia, effects in certain neurological disorders, such as Parkinson's Disease, depression, certain endocrine disturbances and tissue protection following hypoxia/anoxia such as in stroke or myocardial infarction, or an increased level of intracranial pressure or other conditions treatable with GHB.

The invention first provides a pharmaceutical composition of GHB rendered chemically stable and/or resistant to microbial growth in an aqueous medium. Preferred GHB salts of the present invention include sodium, ammonium and calcium. As used herein in certain embodiments, "stable" may mean resistant to degradation of GHB into its known or unknown decomposition elements. The level of GBL that is acceptable can be up to 0.1% of the formulation as per the ICH guidelines for shelf-life determination, As used herein in certain embodiments, "resistant to microbial growth" or "resistant to microbial challenge" means that the formulations meet the criteria set by the Food and Drug Administration and the U.S. Pharmacopoeia for products made with aqueous bases or vehicles, which for bacteria means not less than a 1.0 log reduction from the initial count at 14 days, and no increase from the 14 days count at 28 days, and for yeast and molds, no increase from the initial calculated count at 14 and 28 days. As used herein in certain embodiments, an "aqueous medium" may mean a liquid comprising more than about 50% water. In certain preferred embodiments, an "aqueous medium" may be a solution, suspension, gel or emulsion of GHB, with a solution of GHB being most preferred. Preferred gels are thixotropic gels. Compositions that are resistant to microbial growth are created by dissolving or mixing GHB in an aqueous medium to a concentration or content of greater than of about 150 mg/ml GHB to the maximal solubility of GHB. The solubility of GHB is up to about 750 mg/ml at room temperature (20° C. to about 25° C.), however, heating the aqueous medium during preparation up to 100° C. will increase GHB solubility to at least about 1000 mg/ml. A preferred concentration or content of GHB is about 500 mg/ml.

The amount of GHB that may be mixed or dissolved into an aqueous medium and still be resistant to microbial growth depends upon the pH of the aqueous medium. In certain embodiments the presence of a preservative may allow the amount of GHB contained in the compositions of the present invention to be increased and still maintain resistance to chemical degradation and/or microbial growth. In one embodiment of the present invention, the pH of the aqueous medium of the pharmaceutical composition is about 3 to about 10.

In a preferred embodiment, the pH of said aqueous medium is about 6 to about 7.5. The pH may be from about 3.0 to about 10.3, namely of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, or about 10.3, and all pH values between each of the listed pH values, of the aqueous media. This will produce a GHB composition that is resistant to microbial growth as defined by the test described herein. As used herein, the term "about" generally means within about 10–20%.

These pH values will produce compositions resistant to microbial growth in an aqueous medium if the amount of GHB added, admixed, or dissolved is from above about 150 mg/ml to about 450 mg/ml, namely, above about 150 mg/ml, about 160 mg/ml, about 170 mg/ml, about 180 mg/ml, about 190 mg/ml, about 200 mg/ml, about 210 mg/ml, about 220 mg/ml, about 230 mg/ml, about 240 mg/ml, about 250 mg/ml, about 260 mg/ml, about 270 mg/ml, about 280 mg/ml, about 290 mg/ml, about 300 mg/ml, about 310 mg/ml, about 320 mg/ml, about 330 mg/ml, about 340 mg/ml, about 350 mg/ml, about 360 mg/ml, about 370 mg/ml, about 380 mg/ml, about 390 mg/ml, about 400 mg/ml, about 410 mg/ml, about 420 mg/ml, about 430 mg/ml, about 440 mg/ml, to about 450 mg/ml, and all amounts of GHB between the values listed.

At the medium to high end of the concentration or content of GHB that may be dissolved or mixed in the aqueous medium, the maximal pH that may be used is reduced at room temperature. This is shown in FIG. 1, a graphical presentation of acceptable formulation ranges. At a concentration or content of about 450 mg/ml GHB, the pH may be of about 3.9 to about 10.3. At a concentration or content of about 500 mg/ml GHB, the pH may be of about 4.75 to about 10.3. At a concentration or content of about 600 mg/ml GHB, the pH may be of about 6.1 to about 10.3. At a concentration or content of about 750 mg/ml GHB, the pH may be of about 7.0 to about 10.3. Of course, all pH and concentration or content values in between each of the listed pH and concentration or content values are encompassed by the invention.

Certain embodiments may be selected as sub-ranges from these values of GHB content and aqueous medium pH. For example, a specific embodiment may be selected as a content of about 170 mg/ml to about 440 mg/ml GHB in an aqueous medium, at a pH range of about pH 5.5 to about pH 8.7. Another example of how a range may be selected in an embodiment would be the selection of a content of about 155 mg/ml of GHB, which is a value between the above listed values, to a content of about 350 mg/ml of GHB, and the selection of a pH range of the aqueous medium, such as a pH range of about 8.87, which is a value between the listed pH values, to a pH of about 8.93, which is another value between the listed values of pH. A third example of ranges that may be selected for a specific embodiment would be selection of a single content or concentration of GHB, such as about 200 mg/ml of GHB, and the selection of a pH range, such as a pH of about 3.5 to about 8.2. A fourth example of ranges that may be selected for a specific embodiment would be selection of a content or concentration of GHB over a range, such as about 300 mg/ml to about 400 mg/ml, and the selection of a single pH value for the aqueous medium, such as a pH of about 3. Another example of a range selected for an embodiment may be the selection of a single content or concentration of GHB, such as 400 mg/ml GHB, and a single pH value of the aqueous medium, such as pH 7.7.

Other examples of how a range of an embodiment of GHB content or concentration may be selected include a range of GHB content or concentration from about 200 mg/ml to about 460 mg/ml GHB, encompassing the ranges for GHB described herein, and a range of pH for the aqueous medium may be from about pH 4.3 to about pH 7, encompassing ranges for GHB in an aqueous medium at room temperature described herein. Another example would be the selection of a range of GHB content or concentration from about 153 mg/ml to about 750 mg/ml, and a pH range of about 7 to about 9, encompassing ranges between the listed values of GHB content and pH described herein. An example may be the selection as a GHB concentration or content of about 170 mg/ml to about 640 mg/ml in an aqueous medium, at a pH range of about pH 6.5 to about pH 7.7. Another example of how a range may be selected in an embodiment would be a content or concentration of about 185 mg/ml of GHB, which is a value between the listed values, to a content or concentration of about 750 mg/ml of GHB, at a pH range of about 7.87, which is a value between the listed pH values, to a pH of about 8.91, which is another value between the listed values of pH. An additional example of ranges that may be selected for a specific embodiment would be a content or concentration of about 200 mg/ml of GHB at a pH of about 7 to about 8.2. Another example of ranges that may be selected for a specific embodiment would be a content or concentration of about 750 mg/ml to about 400 mg/ml at a pH of about 7. Another example of ranges that may be selected for a specific embodiment would be a content or concentration of about 300 mg/ml to about 750 mg/ml at a pH of about 8.5 to about 7. Another example of ranges that may be selected for a specific embodiment would be a content or concentration of about 400 mg/ml to about 600 mg/ml at a pH of about 9 to about 5.8. And so forth. Thus, all ranges of pH and GHB concentration or content that can be selected from the values herein and as would be understood by those of ordinary skill in the art, are encompassed by the present invention.

The chemical stability of GHB is affected by pH, with compositions of GHB in an aqueous medium with a pH below about 6 being less effective in maintaining the chemical stability of GHB. Compositions with a pH of greater than about 6.0 are preferred to produce chemically stable formulations of GHB. Thus, a preferred range to produce chemically stable GHB would be from about pH 6 to about pH 9. However, all concentrations or content of GHB in an aqueous medium, as described herein, and as would be understood by those of ordinary skill in the art, may be selected to produce compositions of the present invention.

Additionally, the ranges described above are for a composition at room temperature, which is defined herein as from about about 20° C. to about 25° C., namely, about 20° C. about 21° C., about 22° C., about 23° C., about 24° C., to about 25° C. Within the values and ranges of pH described above, the ranges of concentration or content of GHB may increase at temperatures greater than room temperature. Thus, the maximal content or concentration of GHB in an aqueous medium at a temperature of from about 26° C. to about 100° C., namely about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., to about 100° C., may be from about 750 to about 1 g/ml, namely to about 751 mg/ml, about 760 mg/ml, about 770 mg/ml, about 780 mg/ml, about 790 mg/ml, about 800 mg/ml, about 810 mg/ml, about 820 mg/ml, about 830 mg/ml, about 840 mg/ml, about 850 mg/ml, about 860 mg/ml, about 870 mg/ml, about 880 mg/ml, about 890 mg/ml, about 900 mg/ml, about 910 mg/ml, about 920 mg/ml, about 930 mg/ml, about 940 mg/ml, about 950 mg/ml, about 960 mg/ml, about 970 mg/ml, about 980 mg/ml, about 990 mg/ml, to about 1000 mg/ml. At temperatures below room temperature, the solubility of GHB may decrease, and compositions at lower temperature and solubility of GHB at the pH values and ranges described herein are also encompassed by the invention. Additionally, differences of atmospheric pressure may also increase or decrease the solubility of GHB within the ranges described, and embodiments of the invention with an increased or decreased content of GHB due to changes in pressure are also encompassed by the invention. Of course, it is understood that the present invention encompasses embodiments of GHB concentration or content in an aqueous medium at higher or lower temperature within the values described herein, such as about 980 mg/ml to about 200 mg/ml at 95° C. GHB at a pH of about 9 to about 7.5. Or about 150 mg/ml GHB at about 17° C. at about pH 6 to about pH 7. And so forth. Thus, all ranges of pH and GHB content that can be selected at various temperatures and pressures from the values above, and as would be understood by those of ordinary skill in the art, are encompassed by the present invention.

In certain other embodiments of the present invention, the pharmaceutical composition may comprise a pH adjusting or buffering agent. Such agents may be acids, bases, or combinations thereof. In certain embodiments, the acid may be an organic acid, preferably a carboxylic acid or alphahydroxy carboxylic acid. In certain other embodiments, the acid is selected from the group including, but not limited to, acetic, acetylsalicylic, barbital, barbituric, benzoic, benzyl penicillin, boric, caffeine, carbonic, citric, dichloroacetic, ethylenediaminetetra-acetic acid (EDTA), formic, glycerophosphoric, glycine, lactic, malic, mandelic, monochloroacetic, oxalic, phenobarbital, phenol, picric, propionic, saccharin, salicylic, sodium dihydrogen phosphate, succinic, sulfadiazine, sulfamerazine, sulfapyridine, sulfathiazole, tartaric, trichloroacetic, and the like, or inorganic acids such as hydrochloric, nitric, phosphoric or sulfuric, and the like. In a preferred embodiment, the acid is malic or hydrochloric acid. In certain other embodiments, the pH adjusting agent may be a base selected from the group including, but not limited to, acetanilide, ammonia, apomorphine, atropine, benzocaine, caffeine, calcium hydroxide, cocaine, codeine, ephedrine, morphine, papaverine, physostigmine, pilocarpine, potassium bicarbonate, potassium hydroxide, procaine, quinine, reserpine, sodium bicarbonate, sodium dihydrogen phosphate, sodium citrate, sodium taitrate, sodium carbonate, sodium hydroxide, theobromine, thiourea or urea. In certain other embodiments, the pH adjusting agent may be a mixture of more than one acid and/or more than one base. In other preferred embodiments, a weak acid and its conjugate base are used to form a buffering agent to help stabilize the composition's pH.

In certain embodiments, the composition may contain one or more salts. A "salt" is understood herein to mean certain embodiments to mean a compound formed by the interaction of an acid and a base, the hydrogen atoms of the acid being replaced by the positive ion of the base. Various salts, including salts of GHB, are also encompassed by the invention, particularly as pH adjusting or buffering agents. Pharmaceutically acceptable salts, include inorganic acids such as, for example, hydrochloric or phosphoric acids, or such organic acids as malic, acetic, oxalic, tartaric, mandelic, and the like. Salts formed can also be derived from inorganic bases such as, for example, sodium, potassium, silicates, ammonium, calcium, or ferric hydroxides, and such organic bases as isopropylamine, trimethylamine, histidine, procaine and the like. Alkali met al salts, such as lithium, potassium, sodium, and the like may be used, preferably with an acid to form a pH adjusting agent. Other salts may comprise ammonium, calcium, magnesium and the like. In one embodiment, a salt of GHB comprising an alkali met al may be combined with an acid to create a composition that achieves the desired pH when admixed with an aqueous medium. In another embodiment, a weak base may be combined with GHB to create a composition that achieves the desired pH when admixed with an aqueous solution. Of course, other salts can be formed from compounds disclosed herein, or as would be known to one of ordinary skill in the art, and all such salts are encompassed by the invention.

In certain embodiments, excipients may be added to the invention. An "excipient" as used herein shall mean certain embodiments which are more or less inert substances added as diluents or vehicles or to give form or consistency when the remedy is in a solid form, though they may be contained in liquid form preparations, e.g. syrups, aromatic powders, honey, and various elixirs. Excipients may also enhance resistance to microbial growth, and thus act as a preservative. Such excipients include, but are not limited to, xylitol, mannitol, lactose, starch, magnesium stearate, sodium saccharine, cellulose, cellulose derivatives, magnesium carbonate and the like.

In certain embodiments, the pharmaceutical composition may contain a preservative. A "preservative" is understood herein to mean certain embodiments which are substances added to inhibit chemical change or microbial action. Such preservatives may include, but are not limited to, xylitol, sodium benzoate, methylparaben, propyl gallate BP, sorbic acid, chlorobutanol, dihydroacetic acid, monothioglycerol, potassium benzoate, propylparaben, benzoic acid, benzalkonium chloride, alcohol, benzoic acid, benzalkonium chloride, benzethonium chloride, benzyl alcohol, butylparaben, cetylpyridinium chloride, ethylenediamine, ethylparaben, ethyl vanillin, glycerin, hypophophorus acid, methylparaben, phenol, phenylethyl alcohol, phenymercuric nitrate, propylparaben, sassafras oil, sodium benzoate, sodium propionate, thimerosal and potassium sorbate. Preferred preservatives may be selected from the group comprising, but not limited to, xylitol, sodium benzoate, methylparaben, propylparaben and potassium sorbate. Xylitol is particularly preferred in certain compositions of the invention, because it acts as an preservative and a sweetener, is a caries preventative, is less laxative than other sweeteners, and is recommended for diabetics.

In certain embodiments, the pharmaceutical composition may also contain an antioxidant. An "antioxidant" is understood herein to mean certain embodiments which are substances that inhibits oxidation. Such antioxidants include, but are not limited to, asocrbyl palmitate, butylated hydroxyanisole, butylated hydroxytoluene, potassium metabisulfite, sodium metabisulfite, anoxomer and maleic acid BP.

In certain embodiments, the pharmaceutical composition may also contain a flavoring agent. A "flavoring agent" is understood herein to mean certain embodiments which are substances that alters the flavor of the composition during oral consumption. A type of "flavoring agent" would be a sweetener. Preferred sweeteners or flavoring agents would be microbially non-metabolizable. Especially preferred sweeteners or flavoring agents would be carbohydrates such as xylitol and sorbitol. Such flavoring agents include, but are not limited to, acacia syrup, anethole, anise oil, aromatic elixir, benzaldehyde, benzaldehyde elixir-compound, caraway, caraway oil, cardamom oil, cardamom seed, cardamom spirit, cardamom tincture-compound, cherry juice, cherry syrup, cinnamon, cinnamon oil, cinnamon water, citric acid, citric acid syrup, clove oil, coca, coca syrup, coriander oil, dextrose, eriodictyon, eriodictyon fluidextract, eriodictyon syrup-aromatic, ethyl acetate, ethyl vanillin, fennel oil, ginger, ginger fluidextract, ginger oleoresin, glucose, glycerin, glycyrrhiza, glycyrrhiza elixir, glycyrrhiza extract, glycyrrhiza extract-pure, glycyrrhiza fluidextract, glycyrrhiza syrup, honey, non-alcoholic elixir, lavender oil, citrus extract or oil, lemon oil, lemon tincture, mannitol, methyl salicylate, nutmeg oil, orange-bitter-elixir, orange-bitter-oil, orange flower oil, orange flower water, orange oil, orange peel-bitter, orange-peel-sweet-tincture, orange spirit-compound, compound, orange syrup, peppermint, peppermint oil, peppermint spirit, peppermint water, phenylethyl alcohol, raspberry juice, raspberry syrup, rosemary oil, rose oil, rose water, saccharin, saccharin calcium, saccharin sodium, sarsaparilla syrup, sorbitol solution, spearmint, spearmint oil, sucrose, syrup, thyme oil, tolu balsam, tolu balsam syrup, vanilla, vanilla tincture, vanillin or wild cherry syrup.

Salts, excipients, pH adjusting agents such as acids, bases and buffering agents, flavoring agents, and other agents that may be combined with the compositions of the present invention, or may be used to prepare the compositions of the present invention, are well known in the art, (see for example, "Remington's Pharmaceutical Sciences" 8th and 15th Editions, and Nema et al., 1997, incorporated herein in their entirety), and are encompassed by the invention.

In certain other embodiments, the pharmaceutical composition comprises GHB, a pH adjusting or buffering agent, and an aqueous medium, wherein the components are admixed (sequentially or simultaneously) to prepare said pharmaceutical composition. The pH adjusting or buffering agent and aqueous medium may be any described herein.

The invention also provides a method of preparing a chemically stable and microbial growth-resistant pharmaceutical composition for the treatment of a condition responsive to GHB, comprising admixing GHB and a pH-adjusting or buffering agent in an aqueous medium. In certain embodiments, the method of preparing the pharmaceutical composition further comprises admixing a preservative with the pharmaceutical composition. Other components, such as flavoring agents, salts, and the like, may be added to the composition. The pH adjusting or buffering agent, aqueous medium, preservative, flavoring agents, salts, or other ingredient may be any described herein.

In certain other embodiments, the method of preparing the pharmaceutical composition comprises admixing GHB, a pH adjusting or buffering agent, and an aqueous medium soon before administration to a patient suspected of having a condition responsive to GHB.

The invention also provides a method of treating any therapeutic category of disorder responsive to GHB, comprising administering to a patient suspected of having such a condition a therapeutic amount of a pharmaceutical composition comprising chemically stable GHB (e.g. 1–10 gms.) in an aqueous medium resistant to microbial growth. In certain embodiments, the method of treating a condition responsive to GHB comprises a patient taking a first dosage of from about 0.1 g to about 10 g, namely about 0.1, about 0.2 about 0.3 about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, to about 10 grams of GHB, or as needed by the patient as would be recognized by one of skill in the art. Of course, it will be understood that all values in between those listed, such as 9.45 grams, 6.32 grams, etc. may be administered, and those values are encompassed well. In preferred embodiments, the first dose is administered within an hour of sleep. In preferred embodiments, a second dose of GHB within the values described above may be administered. This second dose is administered preferably within about 2.0 to about 5.0 hrs, namely about 2.0, about 2.1, about 2.2, about 2.3, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, to about 5.0 hours after the first dose, though it may be administered at a time outside of the preferred range.

In certain embodiments, a second pharmaceutical may be administered with the composition of GHB. Such a second pharmaceutical may be e.g., a stimulant administered within the same 24 hour period as the first dose of GHB. The stimulant may be, e.g., but not limited to, methylphenidate or pemoline to counter the residual effects of GHB treatment during periods of wakefulness. In certain embodiments, the method of treating a sleep disorder may include the discontinuation of other second pharmaceuticals used to control a sleep disorder. Such second pharmaceuticals may include, but are not limited to, a tricyclic antidepressant.

In certain embodiments, the invention provides a method of treating any appropriate therapeutic category of disorder, by administration of GHB compositions of the present invention as described above for the treatment of sleep disorders. When GHB is used in methods of treating any therapeutic category of disorder, the GHB composition of the present invention may be mixed with the aqueous medium, and optionally pH adjusting or buffering agent or other additives, by the patient or administrator soon before consumption. The patient may prepare the composition within a few minutes to hours before administration. Alternatively, one or more of the components may be premixed for ready use. The components of the GHB composition of the present invention, GHB, an aqueous medium, pH adjusting or buffering agent, excipients, preservatives, flavoring agents, and/or other components or additives may be stored in a container means suitable to aid preservation. Preferably, the container means is in the form of a set. A "set" as used herein certain embodiments is one or more components of the composition packaged in a container or other suitable storage means.

The present invention also provides a set for the treatment of a condition responsive to GHB comprising, in suitable storage means, GHB and a pH adjusting or buffering agent. In certain embodiments, the GHB and the pH adjusting or buffering agent are separately packaged. In certain other embodiments the GHB and the pH-adjusting or buffering agent may be mixed. The set may contain an aqueous medium. In certain other embodiments, at least one component selected from the group including, but not limited to, GHB, the pH-adjusting or buffering agent and/or an aqueous medium is separately packaged. In certain other embodiments, at least two of the components selected from the group comprising GHB, a pH adjusting or buffering agent and an aqueous medium are mixed together. In some embodiments, the set further contains a preservative. Such a set may have one, two, or more components from the group comprising GHB, a pH-adjusting or buffering agent, an aqueous medium or a preservative packaged separately. Such a set may have two or more components mixed together. Thus, both liquid and dry formulations of GHB and other components may be packaged in a set for mixing before administration, or one or more components may be premixed and packaged together with other components, or all the components may be premixed and packaged in a set.

It is understood that the compositions of the present invention, including those in a set, may be dispersed in a pharmaceutically acceptable carrier solution as described below. Such a solution would be sterile or aseptic and may include water, co-solvent vehicle buffers, isotonic agents, pharmuceutical aids or other ingredients known to those of skill in the art that would cause no allergic or other harmful reaction when administered to an animal or human subject. Therefore, the present invention may also be described as a pharmaceutical composition of GHB with increased stability in a pharmaceutically acceptable carrier solution.

Unless defined otherwise, all technical and scientific terms used herein have the same meaning as commonly understood by one of ordinary skill in the art to which this invention belongs. Also as used herein, the term "a" "an" or "the" is understood to include the meaning "one or more". Although any methods and materials similar or equivalent to those described herein can be used in the practice or testing of the present invention, the preferred methods and materials are now described.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. The Range of Gamma-Hydroxybutyrate's Resistance to Microbial Growth and Chemical Stability in Aqueous Solution. The ordinate is the pH of solutions of GHB. The axis is the concentration (mg/ml) of GHB in aqueous solution. The region below the diagonal line [/] is the range of GHB solubility at room temperature. Greater solubility can be achieved, up to 1 g/ml, by heating the solution up to 100° C. Three solutions were adjusted with HCl and were susceptible to microbial growth (Δ). Two solutions were pH adjusted with malic acid and were resistant to microbial growth (●). Of these two solutions, the one at pH 6 contained xylitol as an excipient. Three solutions were pH adjusted with hydrochloric acid and were resistant to microbial growth (▲). One solution was not pH adjusted and was susceptible to microbial growth (*).

DESCRIPTION OF ILLUSTRATIVE EMBODIMENTS

I. Formualations of Gamma-Hydroxzybutyrate

A. Microbial Growth and Gamma-butyrolactone Formation

The present invention arises from the discovery of chemically stable and microorganism resistant formulations of GHB in an aqueous medium, preferably a solution, and the efficacy of these formulations in the treatment of therapeutic categories of disorders, such as narcolepsy and other sleep disorders. Specifically, GHB is prepared at a concentration greater than about 150 mg/ml in an aqueous medium, up to the limits of GHB's solubility or retention in an aqueous medium, to produce the compositions of the present invention.

The maximum solubility of GHB is affected by the pH of the aqueous medium. At about pH 4, the maximum amount of sodium-GHB that can be dissolved is about 450 mg/ml. The value of pH that is conducive to GHB solubility increases, as is shown at FIG. 1, so that the minimal pH that will dissolve 750 mg/ml GHB was found to be about pH 6.8. This is shown in Table 1.

TABLE 1

Limits of Sodium Oxybate Solubility

| ID | Sodium Oxybate Maximum Solubility | pH of Solution | Temperature |
|---|---|---|---|
| A | | | |
| B | 450 mg/cc | pH 4 (HCl) | 25° |
| C | 500 mg/cc | pH 5 (HCl) | 25° |
| D | 600 mg/cc | pH 6 (HCl) | 25° |
| E | 750 mg/cc | pH 6.8 (HCl) | 25° |
| F | 750 mg/cc + | pH 10.3 | 25° |
| G | 1000 mg/cc | pH unadjusted | 65° Soluble, 25° Gel |

The pH of the aqueous medium also affects the resistance of the composition to microbial growth at about 500 mg/ml GHB. GHB at this concentration in an aqueous medium that is between about pH 5 and pH 9 is resistant to microbial growth, with compositions at about pH 6 to about pH 7.5 being particularly resistant to microbial growth. However, at concentrations of GHB greater than about 750 mg/ml above about pH 7.5, the resistance to microbial growth is reduced. This is shown at Table 2.

TABLE 2

Microbial Challenge Data Summary

| ID | Sodium Oxybate Concentration | pH of Solution | Microbial Challenge Result |
|---|---|---|---|
| H | | | |
| I | 750 mg/cc | 7.5 (HCl) | pass |
| J | 500 mg/cc | 6.0 (HCl) | pass |
| K | 500 mg/cc + Excipients (Xylitol) | 6.0 (Malic Acid) | pass |
| L | 500 mg/cc | 9.0 (HCl) | pass (borderline aspergillus) |

TABLE 2-continued

Microbial Challenge Data Summary

| ID | Sodium Oxybate Concentration | pH of Solution | Microbial Challenge Result |
|---|---|---|---|
| H | | | |
| M | 150 mg/cc (BDL 1995) | 5.0 (HCl) | fail (aspergillus only) |
| N | 150 mg/cc (BDL 1995) | 7.0 (HCl) | fail (aspergillus & staph) |
| O | 150 mg/cc (BDL 1995) | 3.0 (HCl) | fail (aspergillus only) |
| P | 150 mg/cc (BDL 1995) | 10.3 (unadjusted) | fail (aspergillus and staph) |
| Q | 500 mg/cc | 6.0 (Malic Acid) | discontinued |
| R | 500 mg/cc | 7.5 (Malic Acid) | pass |
| S | 500 mg/cc (May '98) | 9.0 (Malic Acid) | discontinued |
| T | 500 mg/cc (May '98) | 7.5 (HCl) | pass* |
| U | Others: 200 mg/cc–800 mg/cc | 5.0–9.0 | pending |

*pass is generally defined as:

For Category 1C Products

| | |
|---|---|
| Bacteria: | Not less than 1.0 log reduction from the initial cout at 14 days, and no increase from the 14 days' count at 28 days. |
| Yeast and Molds: | No increase from the initial calculated count at 14 and 28 days. |

The data from Table 1 and Table 2 are graphically shown in FIG. 1. The concentration of GHB in the composition, when evaluated in relationship to the pH, affects the resistance of the GHB composition to microbial challenge. Compositions of GHB at or below 150 mg/ml are poorly resistant to microbial challenge from a pH range of about pH 3 to about pH 9. However, concentrations of GHB of greater than about 150 mg/ml, up to about 1000 mg/ml of GHB, are believed to be suitably resistant to microbial contamination at these pH ranges.

The chemical stability of GHB is affected by pH. Accordingly, the method for preparing GHB, as described herein, particularly as disclosed in the specific examples, varies with pH. GBL begins to form if the pH is about 6 or less. Compositions with a pH of greater than about 6.0 are preferred to produce chemically stable formulations of GHB. Thus, a preferred range to produce chemically stable GHB would be from about pH 6 to about pH 9. However, any pH or range of pH values where a clinically acceptable amount of GBL is produced is also contemplated as being preferred, and is encompassed by the present invention. The range of GBL could be regulatorily broadened with availability of sufficient toxicological data.

In certain embodiments of the invention, a pH-adjusting agent may be added to the composition. The choice of a pH adjusting agent may affect the resistance to microbial challenge and/or the stability of GHB, as measured by the reduction in assayable GHB. Compositions of GHB, pH adjusted with malic acid are resistant to both microbial growth and chemical degradation of GHB, and are preferred. Other pH adjusting or buffering agents may be selected. Agents that adjust pH that are selected on this basis will undergo a taste testing study. However, any pH adjusting agent disclosed herein or as would be known to one of ordinary skill in the art is contemplated as being useful in the invention. Of course, any salt, flavoring agent, excipient, or other pharmaceutically acceptable addition described herein or as would be known to one of ordinary skill in the art is contemplated as being useful in the inventions Any of the above formulations may be prepared and/or packaged as a powdered or dry form for mixing with an aqueous medium before oral administration, or they may be prepared in an aqueous medium and packaged. After mixing with an aqueous medium, preferrably to prepare a solution, these formulations are resistant to both microbial growth and chemical conversion of GHB to GBL, thereby increasing the shelf-life of therapeutic formulations of GHB in an aqueous medium. These formulations then provide an easily titratable liquid medium for measuring the dosage of GHB to be administered to a patient. Additional embodiments of the composition and methods of preparation are described below and in the examples.

B. Pharmaceutical Compositions

1. Pharmaceutically Acceptable Carriers

Aqueous compositions of the present invention comprise an effective amount of GHB dissolved or dispersed in a pharmaceutically acceptable carrier and/or an aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Insofar as any conventional media or agent is incompatible with the active ingredient, its use in the therapeutic compositions is not appropriate. Supplementary compatible active ingredients can be incorporated into the compositions. For human administration, preparations should meet sterility, pyrogenicity, general safety and purity standards as required by the Food and Drug Administration (FDA).

The GHB may be lyophilized for more ready formulation into a desired vehicle where appropriate. The active compounds may be formulated for parenteral administration, e.g., formulated for injection via intravenous, intraarterial, intramuscular, sub-cutaneous, intralesional, intraperitoneal or other parenteral routes. The preparation of an aqueous composition that contains a GHB agent as an active component or ingredient will be known to those of skill in the art in light of the present disclosure. Typically, such compositions can be prepared as injectables, either as liquid solutions or suspensions. Solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including, e.g., aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free acid or pharmacologically acceptable salts can be prepared in water suitably mixed with hydroxypropylcellulose and/or a pharmacueutically acceptable surfactant. Dispersions can also be prepared in glycerol, liquid polyethylene glycols, and mixtures thereof as well as in oils. Under ordinary conditions of storage and use, these preparation may best contain a preservative to further prevent the growth of microorganisms.

A GHB composition of the present invention can be formulated into a composition in a neutral or salt form. Such salts can be formed from any of the acids and bases described herein particularly depending on the particular GHB or GHB salt used, or as would be known to one of ordinary skill in the art.

The carrier can also be a solvent or dispersion medium containing, for example, water, ethanol, polyol (for example, glycerol, propylene glycol, and liquid polyethylene glycol, or the like), suitable mixtures thereof, and vegetable oils. The proper fluidity can be maintained, for example, by the use of a substance, such as lecithin (e.g. a coating), by the maintenance of the required particle size in the case of dispersion and by the use of surfactants. The prevention of the action of microorganisms can be brought about by any of the preservatives described herein, or as would be known to one of ordinary skill in the art, including various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent (although DMSO may not now be a permitted human drug) is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active GHB may be formulated within a therapeutic mixture to comprise about 100 to about 10,000 milligrams per dose. Multiple doses can also be administered.

In addition to the compounds formulated for parenteral administration, such as intravenous or intramuscular injection, other pharmaceutically acceptable forms include, e.g., tablets or other solids; liposomal formulations; time release capsules; and any other form currently used, including cremes, which then may be admixed with an aqueous medium for oral administration.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5, though other pH ranges disclosed herein the specific examples, such as pH 3 to about pH 9, or pH 6 to about 7.5, are contemplated. In addition, preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

The perferred oral formulations may include such normally employed excipients, as, for example, pharmaceutical grades of xylitol, mannitol, lactose, starch, magnesium stearate, sodium saccharin, cellulose, magnesium carbonate and the like. These compositions can take the form of solutions, suspensions, tablets, pills, capsules, sustained release formulations or powders to be admixed with an aqueous medium. In certain defined embodiments, oral pharmaceutical compositions will comprise an inert diluent or assimilable edible carrier, or they may be enclosed in hard or soft shell gelatin capsule, or they may be compressed into tablets, or the GHB may be packaged separately from or in combination with the excipients, salts, flavorings or any other components described herein, to be admixed with an aqueous medium for oral or injectable formulations, or they may be incorporated directly with the food (i.e. a beverage) of the diet.

For oral therapeutic administration, the active compounds may be incorporated with excipients and used in the form of tablets, buccal tablets or tabs, troches, capsules, elixirs, suspensions, syrups, wafers, and the like, to be admixed with an aqueous medium. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, nutural as gum tragacanth, acacia, cornstarch, or gelatin or synthetic as polyvinyl acetate; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a natural or synthetic flavoring agent. When the dosage unit form is a capsule for admixing with a specific volume of an aqueous medium, it may contain, in addition to materials of the above type, a liquid carrier. Various other materials may be present as coatings or to otherwise modify the physical form of the dosage unit. For instance, tablets, pills, or capsules may be coated with sugar, natural or synthetic polymers, or both. A syrup or elixir may contain the active compounds, sucrose as a sweetening agent, a preservative, a dye and/or a flavoring.

Additionally, any excipient, salt, acid, pH-mediating, adjusting or buffering compound or agent, flavoring, solution, solvent, dispersion, glycerol, glycol, oil, antibacterial and antifungal agents, antibiotics and antihistamines, binders, disintegrating agents, lubricants, sweetening agents, or any other additive or ingredient from those enumerated above or in the examples, or in any pharmaceutically acceptable composition or carrier described herein, or as would be known by one of skill in the art, is contemplated for use in aqueous mediums or solid forms of the GHB compositions of the invention. One or more of these compositions may be packaged with GHB or packaged separately from GHB prior to consumption. If packaged separately, useful compositions of GHB may be obtained by mixing GHB with the other components with an aqueous medium prior to consumption. Such components may be packaged in a set, described below.

2. Sets

Therapeutic sets of the present invention are sets comprising GHB. Such sets will generally contain, in suitable container, a pharmaceutically acceptable formulation of GHB. The set may have a single container, or it may have distinct container for each component, or distinct container for various combinations of components.

When the components of the set are provided in one or more liquid formulations, the liquid formulation is an aqueous medium, with a sterile aqueous solution being particularly preferred. The GHB compositions may also be formulated into a syringeable composition. In which case, the container means may itself be a syringe, pipette, vial, ampule or other such like apparatus, from which the formulation may be applied to an infected area of the body, injected into an animal, or even applied to and mixed with the other components of the set.

However, the components of the set may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, pouch syringe or other container means, into which the GHB formulation or components thereof are placed, preferably, suitably allocated. The sets may also comprise a second container means for containing a sterile, pharmaceutically acceptable buffer or other diluent.

The sets of the present invention will also typically include a means for containing the vials in close confinement for commercial sale, such as, e.g., injection or blow-molded plastic containers into which the desired vials are retained.

Irrespective of the number or type of containers, the sets of the invention may also comprise, or be packaged with, an instrument for assisting with the injection/administration or placement of the GHB composition within the body of an animal. Such an instrument may be a drinking cup, syringe, pipette, or any such medically approved delivery vehicle.

II. Methods of Treatment With the GHB Compositions

Because GHB has been shown to be effective in treating narcolepsy and sleep disorders (Lee, 1977; Mamelak, 1977; Hoes, 1980; Scharf, 1985; Scrima, 1990; Gallimberti, 1992; Series, 1992; Lammers, 1993), reducing alcohol craving and alcohol withdrawal symptoms, (Gallimberti et al., 1989; Gallimberti et al., 1992; Gessa et al., 1992), reducing opiate withdrawal symptoms (Gallimberti et al, 1994; Gallimberti et al., 1993), reducing pain (U.S. Pat. No. 4,393,236), reducing intracranial pressure in patients (Strong, A. 1984), and increasing growth hormone levels in patients (Gerra et al, 1994; Oyama et al., 1970), the formulations of the present invention are also contemplated to be useful in the treatment of any of these disorders or conditions in patients. GHB has also been used alone as a narcotic in patients with a terminal carcinomatous state. GHB has been used with other analgesics, neuroleptics, or with a subliminal barbiturate dose for use as an anesthesia. GHB has been used in closed cranio-cerebral trauma and as a soporific (U.S. Pat. No. 5,380,937). The inventors contemplate the use of the GHB compositions of the present invention as a narcotic, hypnotic, or as a soporific. The inventors also contemplate the use of the GHB compositions of the present invention in combination with analgesics, neuroleptics or barbiturates for use as an anesthesia. The GHB compositions of the present invention may be prepared and administered by any of the means described herein, particularly those described in the section "Pharmaceutical Compositions" and the examples, or by any means as would be known to those of skill in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preferred Embodiments

XYREM™ CLINICAL TRIALS

The inventors developed a liquid formulation composed of GHB, xylitol, and preservative in water (XYREMTM). Subsequent instability of the preservative in this formulation and a desire to initiate clinical trials in a timely manner led to a change in the formulation to a foil pouch. One clinical trial utilized a twin-pouch dosage form, with one side (pouch 1) of the foil packet containing GHB and the other side (pouch 2) containing the flavoring agents (Xylitol, [NF]; Malic Acid, NF;

Patients were instructed to open the twin-pouch with a scissors, empty the contents into a dosing cup, add 2 ounces of water, snap the lid on the dosing cup, shake to dissolve, and drink the entire contents of the cup. Clinical trials conducted by the inventors have been performed using the twin-pouch dosage form.

However, the inventors have continued development of a liquid solution and have now overcome inherent problems with particular formulations and/or preservatives. The inventors have converted patients currently enrolled in a GHB open-label trial to a liquid solution composed of GHB, malic acid, and water—that is diluted with water immediately prior to oral administration.

The need for a liquid solution dosage form is further evidenced by the range of doses being used in a subsequent GHB open-label trial. Three sizes of pouches were prepared for the GHB open-label trial: 1.5 grams, 3.0 grams, and 4.5 grams. The initial dose for all patients in the GHB open-label trial was 6 grams of GHB nightly in divided doses. Dosage adjustments were permitted in the first two weeks of the trial as indicated for intolerance or lack of efficacy. The investigator was permitted to decrease the dose of GHB to 3 grams or 4.5 grams, or increase the dose to 7.5 grams or 9 grams nightly. After two weeks, further dosage adjustments were made if clinically indicated.

Thirty-five patients had their dose increased, and 16 patients had their dose decreased. Patients in the lowest dose group were disproportionately female and weighed 15 kg less than patients in the other two groups. Current dosing levels are noted below:

TABLE 3

Dosing Levels in the GHB Open-Label Trial

|  | Total | 1.5 gram | 3.0 gram | 4.5 gram | 6.0 gram | 7.5 gram | 9.0 gram |
|---|---|---|---|---|---|---|---|
| Number of Patients | 95 | 0 | 4 | 10 | 39 | 12 | 30 |
| Percent of Patients | 100% | 0% | 4% | 10% | 41% | 13% | 32% |

To achieve these individualized doses, it has been necessary to provide a combination of different dose strengths. This complexity would be very difficult to achieve with a marketed product. In addition, a month's supply of twin-pouches is quite bulky. A liquid formulation allows for ease in dosing adjustment with one dosage form. In addition "child-resistant" packaging has been developed with the liquid formulation.

A number of patients have also complained about the flavor with the twin-pouches. As follow-up the inventors sent questionnaires to participants in the inventors' clinical trial, and performed taste testing in normal volunteers. The questionnaire responses, taste testing results, and the clinical experience in narcolepsy patients of the study administrator have all confirmed that unflavored solutions were acceptable.

The concentration and volume of the GHB solution that the patient administers will be the same irrespective of whether it is dissolved from the pouch or diluted from the liquid. This is illustrated in Chart 1 and Table 4:

Chart 1

Comparison of Liquid Solution to Twin-Pouch

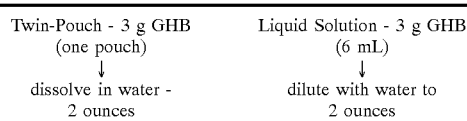

-continued

Chart 1

Comparison of Liquid Solution to Twin-Pouch

| ↓ | ↓ |
|---|---|
| administer solution | administer solution |
| 3 g in 60 mL | 3 g in 60 mL |

TABLE 4

Comparison of Liquid Solution to Twin-Pouch

|  | Twin-Pouch | Liquid Solution |
|---|---|---|
| Amount of GHB | 3 grams (1 pouch) | 3 grams (6 mL) |
| Inactive Components | malic acid<br>xylitol<br>lemon/lime flavor<br>orange flavor | malic acid |
| Final Concentration | 50 mg/mL | 50 mg/mL* |
| Final Volume | 60 mL | 60 mL |

*Final concentration outside the range of the most stable formulation. This formulation strength may be only stable at short periods of time such as 48 hours. The twin pouch version could be solubilized at a a concentration within the preferred range of pH and GHB concentration for longer term storage.

Apart from the elimination of the sweetener (xylitol) and flavoring, the two formulations result in identical solutions.

Conclusions

The concentration and volume of the GHB solution that the patient administers is the same irrespective of whether it is dissolved from the pouch or diluted from the liquid. Either method may be used to produce acceptably stable solutions of GHB.

EXAMPLE 2

Preferred Embodiments

SELF PRESERVING FORMULATIONS OF GAMMA-HYDROXYBUTYRATE SUMMARY OF FORMULATION STUDIES—LIQUID XYREM™

I. Maximum Solubility Range

As seen in FIG. 1 and Table 1, the solubility of GHB varies with pH levels at room temperature (25° C.). Additional amounts of GHB can be solubilized in a gel if heat is applied, in which case a 1000 mg/ml concentration can be achieved. The inventors contemplate that though the concentrations or contents of GHB shown in FIG. 1 and Table 1 are preferred for use, due to the ease of preparing and consuming unheated preparations, higher concentrations of GHB in aqueous medium may also be made, up to 1000 mg/ml.

II. Microbal Testing

The inventors used a three factor analysis involving pH, concentrations of GHB and the pH adjuster used. As seen in FIG. 1, and Table 2, unacceptably low resistance to microbial challenge was seen at 150 mg/ml GHB at pH 3, 5, 7, and 9.0, using HCl as the pH adjusting agent. 150 mg/ml GHB at pH 10.3 without a pH adjusting agent also proved unacceptably resistant to microbial challenge. Borderline acceptable microbial preservativeness was seen in a solution pH adjusted with HCl at 500 mg/ml GHiB at pH 9. At a concentration of 500 mg/ml at pH 6.0 or 7.5, adjusted with either malic acid or HCl, and 500 mg/ml at pH 9.0 adjusted with HCl, the formulation is very effective in a microbial challenge test. The inventors contemplate that a concentration of greater than about 150 mg/ml of GHB, up to the maximal solubility in aqueous solution of GHB, will be suitably resistant to microbial challenge from about pH 3 to pH 10.3. Preferably, the aqueous medium will contain a pH-adjusting or buffering agent.

III. Gamma-Butyrolactone Degradation Range

GBL begins to form if the pH is about 6 or less with the formulation tested thus far.

A. Liquid Formulation Development

The objective of these experiments was to develop a commercial formulation for sodium gamma hydroxybutyric acid. The initial formulation for sodium gamma hydrobutyric acid (GHB) was intended to be an aqueous liquid formulation containing 150 mg/mL GHB, preservatives and flavoring agents. To develop this formulation, studies were conducted to establish the: solubility of the drug in water and as a function of pH, type and concentrations of suitable preservatives, type and concentrations of flavor ingredients, and stability of the formulations.

1. Solubility

The feasibility of preparing formulations containing 150 mg/mL of GHB at pH 3, 5 and 7 was established. Solutions containing 150 mg/mL GHB were prepared. The initial pH was greater than pH 7.5 and the final pH was adjusted to 3, 5 or 7 with hydrocloric acid. The solutions were observed for precipitation and assayed by HPLC for GHB content. The results showed that no precipitation was observed and the drug concentration was found to be 150 mg/mL by HPLC. This information was used as the basis for additional formulation development studies.

2. Preservatives

Preservative effectiveness studies were conducted to identify a suitable preservative for the GHB liquid formulation. The following formulations shown in Table 5 were prepared and tested using *Staphylococcus attreus* (ATCC #6538), *Pseudomonas aeruginosa* (ATCC #9027) and *Aspergillus niger* (ATCC #16404).

TABLE 5

Liquid Formulations Used in Preservative Effectiveness Testing

| Formulation | pH | Sodium Benzoate | Methylparaben Propylparaben | Potassium Sorbate | Control |
|---|---|---|---|---|---|
| 1 | 3 | X | | | |
| 2 | 5 | X | | | |
| 3 | 7 | X | | | |
| 4 | 3 | | X | | |
| 5 | 5 | | X | | |
| 6 | 7 | | X | | |
| 7 | 3 | | | X | |
| 8 | 5 | | | X | |
| 9 | 7 | | | X | |
| 10 | 3 | | | | X |
| 11 | 5 | | | | X |
| 12 | 7 | | | | X |
| 13 | no pH adjustment | | | | X |

The preservative used in each formulation is marked with an X. The results showed that formulations #3, 4, 6 and 9 reduced all three challenge microorganisms by >99.99% in 48 h of contact time. Formulations #1, 5 and 7 reduced all three challenge microorganism by >99.99% in 7 days of contact time. Formulations #2, 8, 10, 11, 12 and 13 did not reduce Aspergillus niger mold to >99.99%, although some reduction occurred in 7 days of contact time. Controls #10, 11, 12 and 13 demonstrated activity against Pseudomonas aeruginosa.

3. Stability

Based on the results of the preservative effectiveness testing, five formulations were selected for stability testing. Table 6 shows the composition of the formulations.

TABLE 6

Liquid Formulations Used in Informal Stability Program

| Chemical | 1 | 2 | 3 | 4 | 5 |
|---|---|---|---|---|---|
| Potassium Sorbate | 0.4 gm | 0.4 gm | | | |
| Sodium Benzoate | | | 1.0 gm | | |
| Methylparaben | | | | 0.36 gm | 0.36 gm |
| Propyl- | | | | 0.04 gm | 0.04 gm | removed from the stability chambers after 1, 2 and 3 months and assayed by high performance liquid chromatography (HPLC) for GHB content. Appearance and pH were also monitored.

Table 7 shows the results for the 3 month time point. Samples stored at 60° C. changed color but samples at all other conditions remained unchanged in color.

The pH of all formulations migrated upward over the three month stability period 60C. The percent increase in pH from initial to 3 months, was greater for the formulations which were initially adjusted to lower values.

For example, the migration of pH in formulations 1,3 and 4 (adjusted down to pH 3) were 21–30 percent across all conditions in three months. The migration of pH in formulations 2 and 5 (adjusted down to pH5) were 4.2–12 percent across all conditions in 3 months. Maintenance of pH becomes important for long term storage since preservatives are known to degrade in formulations having pH levels above approximately pH 6.

Additionally, development of flavor systems to mask the negative taste of perservatives is difficult.

TABLE 7

Table 7
Results of Liquid Formulation Informal Stability Study at Three Months

| Formulation # (See Table 6) | Attribute | 25° C./60% RH Upright | 25° C./60% RH Inverted | 40° C./75% RH Upright | 40° C./75% RH Inverted | 60° C. Upright |
|---|---|---|---|---|---|---|
| 1 Potassium Sorbate (pH 3) at 3 months storage | % t = 0 pH Appearance | 100.7 3.63 clear, colorless | 101.6 3.64 clear, colorless | 101.2 3.84 clear, colorless | NA 3.82 clear, colorless | NA 3.91 clear, light yellow |
| 2 Potassium Sorbate (pH 5) | % t = 0* pH Appearance | 102.1 5.21 clear, colorless | 105.0 5.28 clear, colorless | 104.0 5.55 clear, colorless | 102.0 5.56 clear, colorless | 99.6 5.61 clear, light brown |
| 3 Sodium Benzoate (pH 3) | % t = 0 pH Appearance | 102.4 3.60 clear, colorless | 104.1 3.74 clear, colorless | 99.1 3.78 clear, colorless | 102.6 3.75 clear, colorless | 97.0 3.79 clear, colorless |
| 4 4 Methyl & Propyl Parabense (pH 3) | % t = 0 pH Appearance | 101.5 3.63 clear, colorless | 102.7 3.71 clear, colorless | 100.6 3.81 clear, colorless | 101.2 3.80 clear, colorless | 93.7 3.83 clear, colorless |
| 5 4 methyl & Propyl Prabens (pH 5) | % t = 0 pH Appearance | 103.1 5.22 clear, colorless | 105.8 5.55 clear, colorless | 101.9 5.55 clear, colorless | 103.1 5.56 clear, colorless | 95.6 5.60 clear, light yellow |

*% GHB at t = 0 percent of label claim
**initial time (t = 0)

TABLE 6-continued

Liquid Formulations Used in Informal Stability Program

| Chemical | 1 | 2 | 3 | 4 | 5 |
|---|---|---|---|---|---|
| paraben | | | | | |
| GHB | 30 gm | 30 gm | 30 gm | 30 gm | 30 gm |
| Xylitol | 40 gm | 40 gm | 40 gm | 40 gm | 40 gm |
| Water q.s. | 200 mL | 200 mL | 200 mL | 200 mL | 200 mL |
| Initial pH | 8.68 | 8.68 | 9.30 | 7.75 | 7.75 |
| Formulation Adjusted pH | 3.01 | 5.00 | 3.00 | 2.98 | 4.98 |

The formulations were packaged in 125 mL, amber PET bottles with safety lined child-resistant caps and stored upright and inverted at 60° C., 40° C./75% relative humidity (RH) and 25° C./60% relative humidity. Samples were 4. Liquid Formulation Organoleptic Testing Based on the above stability data and preservative effectiveness testing, a pH 5 formulation containing potassium sorbate was selected as the primary base formulation for flavor system development and organoleptic testing. A pH 3 formulation containing potassium sorbate was selected as the back-up formulation.

B. Dry Powder Formulation Development

Developing a flavor system for the primary and back-up liquid formulations proved to be difficult and a decision was made to develop a dry powder formulation for reconstitution with water before consumption. This approach removed the need for a preservative system, the requirement to adjust pH to levels below pH6, and allowed the development of a suitable flavor system.

1. Dry Powder Formulation Organoleptic Testing

To develop a flavor system for the powder formulation, several parameters were evaluated. The flavor attributes of a GHB solution was characterized by a professional sensory panel. A mimic base containing similar sensory properties as a GHB solution for flavor system was developed. Generally Recognized As Safe (GRAS) excipients for flavor system development were selected. Different excipients (flavorings, sweeteners, acidulants and flow agents) in the mimic base were screened. Three flavor systems for the focus group test were selected. A preferred flavor system was optimized based on comments obtained from the focus group testing. This final formulation with GHB was optimized.

Based on the above activities, the following formulations in Table 8 were selected for stability studies:

TABLE 8

Composition of Prototype Dry Powder Formulation

| Ingredient | Composition (grams) | Purpose |
|---|---|---|
| GHB | 3 | Active |
| Xylitol | 5.5 | non-cariogenic sweetener |
| Malic acid | 0.2 | Acidulant |
| Flavor 1 | 0.2 | Flavor ingredient |
| Flavor 2 | 0.04 | Flavor ingredient |
| Silicon Dioxide (Cab-O-Sil ®) | 0.03 | Flow enhancer |

2. Dry Powder Formulation Stability

A study was initiated to evaluate the stability of the above prototype formulation in two types of foil packages (high and moderate moisture resistant) as well as the stability of GHB alone in one type of foil package (high moisture resistant). Table 9 shows the Lots that were placed on stability. The foil packages were a high moisture resistant pouch and a moderate moisture resistant pouch. The study protocol, Table 10, required the samples to be stored at 40±2° C./75±5% relative humidity for six months, and 25±2° C./60±5% relative humidity for 12 months. Table 11 shows the tests, methods, number of packets/test and specifications for the study.

TABLE 9

Dry Powder Informal Stability Study Package Composition

| Lot Number | Manufacture Date | Package Configuration | Special Comments |
|---|---|---|---|
| SPO #8018 A | 10/06/95 | Foil Packet | Moderate moisture resistant pouch. |
| SPO #8018 B | 10/06/95 | Foil Packet | Highest moisture protection pouch. |
| SPO #8018 C | 10/06/95 | Foil Packet | Drug substance only. Highest moisture protection pouch. |

TABLE 10

Dry Powder Informal Stability Study Protocol

| Storage Conditions | Stability Time in Months | | | | | | |
|---|---|---|---|---|---|---|---|
| | 0 | 1 | 2 | 3 | 6 | 9 | 12 |
| 40 ± 2° C./75% ± 5% RH | | | X | X | X | X | |
| 25 ± 2° C./60% ± 5% RH | X | X | C | C | R | R | R |

X = Samples to be tested
C = Contingency Samples
R = Reduced testing; assay and H$_2$O only
RH = Relative Humidity

TABLE 11

Dry Powder Informal Stability Tests and Specifications

| Test | Method | Packets/Test | Specification Limits |
|---|---|---|---|
| Appearance Dry Material | Visual | Use HPLC | White to off-white free flowing powder |
| Appearance Reconstituted Material | Visual | Use HPLC | Cloudy, off-white solution with visible particulates |
| Rate of Dissolution | Visual | Use HPLC | Material should dissolve completely in five min with mixing |
| Odor | Olfactory | Use HPLC | Characteristic Lemon/Lime odor |
| Assay: GHB | HPLC | 3 | 90.0%–110.0% |
| Assay: Malic Acid | HPLC | Use HPLC | 90.0%–110.0% |
| Impurities/ Degradants | HPLC | Use HPLC | Not more than 1% for any individual impurity/degradant and Not more than 3% total impurity/degradants |
| Vacuum Leak test | Visual | 3 | No Appearance of Leaking |
| pH | USP <791> | Use HPLC | For Information |
| Moisture | Karl Fisher | 3 | Report Value - to be determined |

After two months at 40±2° C./75±5% relative humidity, the potency (% label claim) of Lots SPO 8018A and SPO 8018B was less than 94.0%, the lower limit of the specification, whereas Lot SPO 8018C showed no loss in potency. Lots 8018A and 8018B showed approximately 96% potencies after 2 months at 25° C.±2° C./65%±5% relative humidity. Lot SPO 8018C again showed no loss in potency at this lower storage condition.

3. Appearance

After 2 months at 40° C.±2° C./75%±5% relative humidity, Lots SPO 8018A and SPO 8018B showed significant melting, whereas Lot 8018C showed no melting. Lots SPO 8018A and SPO 8018B also showed partial melting after 2 months at 25° C.±2° C./65%±5% relative humidity. Lot SPO 8018C again showed no evidence of melting at this lower storage condition.

Based on the physical changes in state observed during the stability studies, it was apparent that a solid state interaction between GHB and the excipient blend had occurred. Since xylitol made up the majority of the excipient blend, it was assumed that xylitol was the primary source of the drug-excipient interaction. An alternative hypothesis was also proposed, based on the possibility that the package was mediating the interaction between GHB and xylitol. Three studies were initiated to test these hypotheses.

4. Stability of GHB Solids in a Set Container-System

In the first study, the samples that were stored at 25±2° C./60±5% relative humidity were transferred to glass vials and then stored at 40±2° C./7±5% relative humidity. In the second study, mixtures of GHB and xylitol were gently rubbed between sheets of different types of foil packaging. The mixtures were observed for changes in physical appearance. In the third study, different mixtures of GHB and xylitol were prepared. Differential Scanning Calorimetry (DSC) thermograms were then done to look for changes in the thermograms. The results of these studies are summarized below.

Transfer to Glass: Samples of Lot 8018A and Lot 8018C that were previously stored at 25±2° C./60±5% relative humidity were transferred to amber screw cap vials and stored at 40±2° C./75±5% relative humidity. Analyses similar to those shown in Table 6 were done. After 1 month, the potency of Lot 8018A was 94.6% whereas the potency of Lot 8018C (GHB only) was 100%. In addition, Lot 8018A also showed evidence of melting. The results supported the hypothesis that GHB and xylitol were interacting in the solid state and the interaction appeared to be independent of packaging.

Foil Study: Mixtures of GHB and xylitol were placed between folded sheets of several different foil packaging materials. Slight adhesion of the mixed granules with the foil lining was observed for all of the foils examined. No direct evidence of melting was observed, however, even when excessive force was applied to the outer foil surfaces. This data suggests that the packaging material was not responsible for the solid state interaction observed during the stability studies.

DSC thermographs were obtained for samples of GHB/xylitol containing GHB:xylitol mixtures of 33:66, 45:55 and 55 percent 45 respectively. The scans were conducted at a scan rate of 10° C./min. The thermograms showed that the sample containing GHB:xylitol 33:66 showed a broad endothermic transition starting at 35° C.–40° C. Samples with higher ratios of GHB:xylitol also showed broad endothermic transitions that started at temperatures of 45° C.–50° C. The changes seen in the thermograms supported the hypothesis that a solid state interaction may be occurring between GHB and xylitol that resulted in low potencies for formulations containing mixtures of these two agents.

As a result of the changes seen in the DSC thermograms for different mixtures of GHB:xylitol, a study was initiated to investigate the stability of a formulation containing GHB:xylitol excipient blend 55:45. A formulation containing GHB:xylitol excipient blend 33:66 was used as a control sample. The formulations were packaged in glass vials and stored at 50° C., 40±2° C./75±5% relative humidity and 25±2° C./60±5% relative humidity. The appearance and potency of the formulations were monitored through analyses of stability samples. The stability study also showed potency losses after 1 month at 40° C.±2° C./75±5% relative humidity with both the 50/50 GHB:xylitol ratio as well as the original 33/66 ratio formulation. Partial evidence of melting was also observed in both formulations.

Studies with mixtures of GHB:xylitol excipient blend indicated that the mixture was incompatible in the solid state. However, when prepared as an aqueous solution, these mixtures were chemically compatible. Using this information, a decision was made to package the GHB formulation in dual pouches; one pouch containing GHB alone and the other containing a mixture of xylitol and the other flavor ingredients. The formulation will contain equal amounts of GHB and the excipient blend. This product will be prepared, packaged, and may be checked for stability.

EXAMPLE 3

THE PHARMACOKINETICS OF GAMMA-HYDROXYBUTYRATE

I. Study Objectives

The objective of this study was to assess the pharmacokinetics of GHB after oral administration of two consecutive single doses of GHB (3 g/dose; patients generally ingested the first dose of this medication prior to bedtime and the second dose from 2.5 to 4.0 h later) to narcoleptic patients who are maintained on a chronic regimen of GHB.

II. Study Design

This pharmacokinetic study was conducted as an open-label, single-center investigation in 6 narcoleptic patients. The study design is summarized as follows:

TABLE 12

| Screening/Washout → | Treatment/Blood Sampling → | Follow-up |
| --- | --- | --- |
| (1 or more days to dosing; washout, at least 8 h | (Two 2 g GHB oral doses, 4 h apart; 21 blood samples) | (Within 48 h after last blood sample) |

Narcoleptic patients, 18 years of age or older, who volunteered for this study were screened at least one day prior to the treatment phase. Each patient was determined to be in stable health and evaluated for the presence of narcolepsy, defined for the purposes of this example as one or more years of medical history of narcolepsy as evidenced by a recent nocturnal polysomnogram (PSG) and a valid score from a Multiple Sleep Latency Test (MSLT).

Patients maintained on GHB were allowed to participate. These patients had been weaned from antidepressants, hypnotics, sedatives, antihistamines, clonidine, and anticonvulsants though a stable regimen of methylphenidate (immediate release or sustained release) was allowed. Each patient passed a pre-study physical examination (which included hematology, blood chemistry, urinalysis, and vital signs measurements) prior to the commencement of the treatment phase.

Before oral administration of the first GHB dose, an indwelling catheter was placed in an arm vein and a baseline blood sample was collected. Each patient then ingested a 3 g dose of GHB before bedtime. Another 3 g GHB dose was administered 4 h after the first dose. Twenty-one sequential blood samples were collected over 12 h (starting at 10 min after the first dose and ending at 8 h after the second dose). Upon completion of the treatment phase, a follow-up physical examination which included the measurement of vital signs was performed on each patient within 48 h after the last blood sample. A detailed description of the trial methodology is presented in Section IV.

III. Inclusion Criteria

Patients were included in the study if they: had signed an informed consent prior to beginning protocol required procedures; had not participated in such a study at an earlier date; were willing and able to complete the entire study as described in the protocol; were 18 years of age or older at study entry; had not taken any investigational therapy other than GHB within the 30-day period prior to screening for this study; had an established diagnosis of narcolepsy for at least one year with documentation from a qualified laboratory by a nocturnal polysomnogram (PSG) and a Multiple Sleep Latency Test (MSLT) which demonstrated mean sleep latency to be less than 5 min and REM onset in at least 2 of 5 naps; had not been diagnosed with uncontrolled sleep apnea syndrome, defined as a sleep Apnea Index of 5 or an Apnea Hypopnea Index (AHI) greater than 10 per hour or any other cause of daytime sleepiness; and were free of any medication for their narcolepsy (including hypnotics, sedatives, antidepressants, antihistamines, clonidine, and anticonvulsants) other than GHB and methylphenidate (IR or SR). Patients admitted to this study if they were not experiencing unstable cardiovascular, endocrine, gastrointestinal, hematologic, hepatic, immunologic, metabolic, neurological, pulmonary, and/or renal disease which would place them at risk during the study or compromise the protocol objective; did not have neurological or psychiatric disorders (including transient ischemic attacks, epilepsy, or multiple sclerosis) which, in the investigator's opinion, would preclude the patients' participation and completion of this study; did not have a current or recent (within one year) history of alcohol or drug abuse; did not have a serum creatinine greater than 2.0 mg/dL, abnormal liver function tests (SGOT or SGPT more than twice the upper limit of normal, or serum bilirubin more than 1.5 times normal). Female patients were entered into the study if they were either post-menopausal (i.e. no menstrual period for a minimum of 6 months), surgically sterilized or provided evidence of effective birth control. Females of childbearing potential must agree to continue to use an IUD, diaphragm, or take their oral contraceptives for the duration of the study. Female patients of childbearing potential must have a negative pregnancy test upon entry into the study.

IV. Trial Methodology

A time and events schedule is presented in Table 12.

A. Screening Period/Washout

Six narcoleptic patients who were chronically being treated with GHB were recruited to participate in this pharmacokinetic study. The screening period was at least one day prior to the treatment phase. During the screening period each patient completed the following procedures for the assessment of their physical condition: medical history evaluation; physical examination evaluation; clinical laboratory evaluation; inclusion criteria review. Each patient's GHB and methylphenidate regimen also were recorded on an appropriate case report form (CRF). The investigator also ensured that there was at least an 8-hour washout period for GHB prior to the treatment.

B. Treatment Period/Blood Samples Collection

All patients were hospitalized from approximately four hours prior to first GHB dosing (around 6 p.m.) until the end of the treatment period (around 10 a.m. the next morning). Patients ate their dinner at the clinical research unit soon after arrival and fasted until breakfast next morning. At least three hours elapsed between the completion of dinner and the administration of the first GHB dose. An indwelling catheter was placed in an arm vein of each patient for blood sampling at approximately 30 min and 1 h before the first GHB dose and a baseline blood sample (5 mL) was collected.

The first GHB dose (3 g) was administered at around 10 p.m. Dosing of individual patients were staggered. The second GHB dose was administered at 4 h after the first GHB dose (i.e. immediately after the 4 h blood sample). The exact dosing times in each patient were recorded on appropriate CRF pages. Blood samples (5 mL each) were collected through the indwelling catheter into heparinized tubes at 0.2, 0.4, 0.6, 0.8, 1, 1.5, 2, 3, 4, 4.2, 4.4, 4.6, 4,8, 5, 5.5, 5, 7, 8, 10, and 12 h after the first GHB dose. Blood samples were processed according to the procedures described herein. Patients were monitored for adverse experiences throughout the study according to the specific procedures.

C. Follow-up

Follow-up occurred within 48 h after the last blood sample had been collected. An abbreviated physical examination which included vital signs measurement was performed. Adverse experiences and concomitant medication use, if any, were assessed. Any ongoing adverse experiences and clinically important findings in a patient were followed to the investigator's and/or sponsor's satisfaction before the patient was discharged from the study.

D. Methods of Assessment

1. Medical History

The medical history was recorded during the screening period. The history included gender, age, race, height, prior reaction to drugs, use of alcohol and tobacco, history and treatment, if any, of cardiovascular pulmonary, gastrointestinal, hepatic, renal, immunologic, neurological, or psychiatric diseases and confirmation of inclusion criteria.

2. Physical Examination

Physical Examination included body system review as well as measurement of body weight and vital signs and a neurological examination.

3. Vital Signs

Vital signs measurements included recording of blood pressure, heart rate, respiration, and body temperature.

4. Clinical Laboratory

All clinical laboratory tests were performed at a local laboratory. The laboratory tests and analysis were required of each patient included: hematology, including hemoglobin, hematocrit, red blood cell count, white blood cell count and differential; fasting blood chemistries included blood urea nitrogen (BUN), uric acid, glucose, creatinine, calcium, phosphorus, total protein, albumin, sodium, potassium, SCOT (AST), SGPT (ALT), alkaline phosphatase, lactate dehydrogenase (LDH), and total bilirubin; midstream catch urinalysis included specific gravity, pH, protein, occult blood, ketones and glucose by dipstick determination as well as a microscopic examination of urine sediment for RBC, WBC, epithelial cells or casts or crystals; and a urine pregnancy test, if applicable. Any laboratory parameter that was out of range and considered clinically significant excluded the patient from participation in this study. The investigator would provide an explanation of all observations that were significantly outside the reference range.

5. Concomitant Medication

The continued use of a fixed dose of methylphenidate immediate release or sustained release (IR or SR) is acceptable. The methylphenidate regimen was recorded on the appropriate case report form.

6. Adverse Experiences

An adverse experience are any undesirable event experienced by a patient or volunteer whether or not considered drug-related by the investigator. An undesirable event can be, but is not limited to, subjective symptoms experienced by a patient or, objective findings such as significant clinical laboratory abnormalities. Adverse experience is considered synonymous with the term "adverse event".

The investigators report in detail all adverse experiences and symptoms that occurred during or following the course of trial drug administration for up to 2 days. Included in the description was the nature of the sign or symptom; the date of onset; date or resolution (duration); the severity; the relationship to trial treatment or other therapy; the action taken, if any; and the outcome.

A serious adverse experience is defined as one that is fatal, life threatening, permanently disabling, or which results in or prolongs hospitalization. In addition, overdose, congenital anomaly and occurrences of malignancy are always considered to be serious adverse experiences. An unexpected adverse experience is one not previously reported.

Any serious or unexpected adverse experience (including death) due to any cause which occurs during the course of this investigation, whether or not it is related to the investigational drug, was reported within 24 h by telephone or facsimile. Appropriate authorities were to be informed if the serious or unexpected adverse experience, in the opinion of inventors, was likely to affect the safety of other patients or volunteers or the conduct of the trial.

7. Clinical Supplies-Study Medication

Formulation: Unit 3 g GHB doses (Lot PKI) were obtained from Orphan Medical. Each unit dose comprised twin foil pouches: one pouch containing GHB and the other containing a flavor excipient blend. (Table 8 formulation) Labeling: The clinical supplies for individual patients were packaged in separate containers. Each container included two unit doses, i.e. two twin-pouches. Clinical supplies for eight patients (including those for two replacement patients) were delivered to the investigator. Foil twin-pouches were identified with a two-part label.

Dose Administration: The investigator or designee prepared the oral solution for dosing within 30 min prior to the first oral administration to individual patients. The contents of one twin-pouch was emptied into a dosing cup to which two ounces of water were added. After replacing the lid of the dosing cup, it was gently shaken to dissolve the GHB and excipient in water. The GHB solution was ingested in its entirety. Likewise, the second GHB dosing solution was prepared in the same manner and was ingesting in its entirety at 4 h after the first GHB dose.

Investigational Drug Accountability: At the conclusion of the study, all clinical supplies were accounted for on the drug accountability form and unused drug supplies were returned for proper disposition.

8. Determination of Plasma GHB Concentrations

Plasma samples were analyzed for GHB by the Department of Bioanalytical Chemistry (Covance (previously known as Hazelton Corning), Madison, Wis.) A gas chromatographic method with mass selective detection (GC-MSD) was used in the analysis.

9. Data Management and Analysis

Data Base: An EXCEL data base (spreadsheet) was constructed from data recorded on Case Report Forms (CFR) and plasma GHB concentration data sets received from Covance (Corning Hazleton). Each entry in the EXCEL spreadsheet was checked against the CRFs and any data entry error found was corrected.

Pharmacokinetic Analysis: Pharmacokinetic parameters were determined for individual sets of plasma GHB concentration vs. time data using the non-compartmental routine in WinNonlin Version 1.1. The peak GHB concentrations ($C_{max}$) and the times of their respectively occurrences ($t_{max}$) were observed values. Terminal half-life ($T_{1/2}$) was obtained by log-linear regression analysis of the terminal phase of concentration vs. time curves. The area under the curve ($AUC_{inf}$) and the area under the first moment curve ($AUMC_{inf}$) were calculated by the linear trapezoidal rule up to the last determined concentration and included extrapolated areas to time infinity. Apparent oral clearance (CL/F) was calculated as $Dose/AUC_{inf}$. Volume of distribution (Vz/F) was determined by taking the ratio between CL/F and $\lambda_z$ (elimination rate constant). Mean residence time (MRT) was estimated from the ratio between $AUMC_{inf}$ and $AUC_{inf}$.

Safety Analyses: Results of physical examinations, vital signs, clinical laboratory data were summarized in tabular form and presented by patient number. Adverse events also were tabulated in a similar fashion.

10. Results

Patient and Study Accountability: Six narcoleptic patients were enrolled and all six completed the study in its entirety.

Protocol Compliance: There were no inclusion criteria violations. All patients admitted into the study met the study entrance requirements and completed the screening phase at least one day before the treatment phase.

All six patients took non-study medications in addition to methylphenidate and GHB doses because none of their concomitant medications (Synthyroid, Premarin, Lovastatin, Flovastatin, furosemide, potassium, hydrochlorothiazide, lansoprazole, and verapamil) were on the exclusion list (which included hypnotics, sedatives, antidepressants, antihistamines, clonidine, and anticonvulsants). Adverse experience probes, vital sign measurements, and essentially all pharmacokinetic blood samples were performed at protocol specified times; the few deviations in blood sampling times should not have any impact on the outcome of the study since actual blood sampling times were used in the pharmacokinetic analysis.

The diagnosis of narcolepsy for at least one year in each patient was verified by a nocturnal polysomnogram (NSC) and a Multiple Sleep Latency Test (MSLT) conducted at a qualified laboratory. Five patients have been maintained on GHB nightly for over 10 years and one patient has been receiving GHB nightly for two years. One patient (Subject 101) also had multiple sclerosis; however, the attending physician, judged that it would not interfere with the objective of this study. A few of the screening clinical laboratory results marginally fell outside the reference range but none was considered by the attending physician to be clinically significant.

Exposure to Study Drug: All patients ingested the two GHB doses as scheduled (immediately prior to bedtime). The GHB doses per kg body weight ranged from 26.4 to 52.4 mg/kg.

Plasma GHB Concentration Profiles: It was noted that, in certain cases, (Patients #103, and #106), plasma GHB concentrations did not decline from the first $C_{max}$ to zero concentration at h 4. Upon achievement of the second $C_{max}$, the semi-logarithmic plots of concentration versus time data in Patients #102, #103, and #105 exhibited a convex decline profile. Such a decline pattern suggested non-linear pharmacokinetics. The highest plasma GHB concentration observed in the study was 125.0 lg/mL which occurred in Subject 101 after the second 3 g GHB dose.

Pharmacokinetic Parameter Estimates: The mean (±SD) showed that maximum GHB concentrations ($C_{max}$) were 62.8±27.4 μg/mL and 91.2±25.6 μg/mL for the first and second GHB doses, respectively. The corresponding mean observed times to maximum concentrations were 40±6 and 36±7 min after the first and second GHB doses, respectively. The mean $AUC_{inf}$ was 17732±4603 μg/mL.h. The mean CL/F was 4.2±1 mL/min/kg and the mean $V_z$/F was 307±96 mL/kg. The mean $MRT_{inf}$ was 249±56 min. The mean GHB $T_{1/2}$, estimated by linear regression of log[C] vs. time data of the terminal phase of the second GHB dose was 53±19 min.

Adverse Experiences: No adverse experiences were reported in the study.

Follow-up Safety Assessments: Inspection of screen and follow-up physical examination results per individual patient did not identify any changes attributable to GHB.

11. Discussion

To the inventors' knowledge, the level of GHB in human systemic circulation has not been reported in the literature. Hence, baseline (0 h) plasma samples were analyzed for GHB concentrations. The GC-MSD method used in the present study had a limit of quantification (LOQ) of 7.02 μg/mL and analysis of the baseline plasma samples showed the endogenous levels of GHB are below this sensitivity limit. This finding was confirmed by adding known amounts of GHB (5, 10, and 25 μg per mL of plasma) to blank human plasma samples and subjected these samples to GC-MSD analysis. This method of standard addition allowed an estimation of the endogenous GHB level in human plasma which was found to average about 2.02 μg/mL, (i.e. approximately 2/3 of the Limit Of Quantitation (LOQ) for a validated assay. Hence, the endogenous GHB level was not subtracted from exogenous GHB concentrations prior to pharmacokinetic analysis.

Values of mean $t_{max}$ (~40 min after dosing) and $t_{1/2}$ (~35 min) suggest that the GHB solution administered to narcoleptic patients in this study was readily absorbed and rapidly eliminated. In 3 out of 6 patients the drug was essentially gone from the systemic circulation by h 4 after the first GHB dose whereas in the remaining three patients residual GHB levels of 15 μg/mL was still detected at h 4.

The convex nature of the decline of plasma GHB concentrations in three patients after achievement of the second $C_{max}$ indicated that elimination of GHB from the systemic circulation in these three patients is capacity limited. Nevertheless, it should be noted that plasma GHB concentrations were no longer detectable by h 6 after the second GHB dose (10 h after the first GHB dose). The mean apparent oral clearance found in this study was 4.2±1.0 mL/min/kg and appeared to be comparable to the apparent oral clearance of 5.3±2.2 mL/min/kg reported in the literature for a group of alcohol dependent patients who were administered a dose of 50 mg/kg (Ferrara, 1992). While it appeared that the GHB dose (ranging from 26.4 to 52.4 mg/kg with a mean of 36.5 mg/kg) in the present study was lower than the comparison GHB dose (50 mg/kg) administered to the alcohol dependent patients (Ferrara, 1992), it should be noted that each patient in the present study was administered two consecutive GHB doses at four-hour interval and residual GHB levels were detected in three out of six patients immediately prior to the second GHB dose. The GHB pharmacokinetic non-linearity in alcohol dependent patients easily can be observed from the apparent oral clearance which increased to 8.1±4.8 mL/min/kg when the GHB dose is reduced to 25 mg/kg dose (Ferrara, 1992). In the present study, the non-linearity was less obvious because each narcoleptic patient received two consecutive fixed 3 g doses regardless of body weight.

The mean elimination half-life of GHB in the six narcoleptic patients was determined to be 53±19 min, longer than that in alcohol dependent patients after a 50 mg/kg GHB dose (Ferrara, 1992). The lengthening of GHB elimination half-life observed in this study partially was caused by the wider spacing in sampling time points. However, capacity limited elimination of this drug in some of the narcoleptic patients also could have contributed to this prolongation.

GHB appears to have a shortcoming in that its elimination from the body is capacity limited in some patients when the drug is administered at a fixed regimen of 3 g twice nightly at four-hour interval. However, from a therapeutic perspective, GHB offers an advantage in the treatment of narcolepsy because by the time a patient wakes up in the morning (i.e. 8 to 10 h after the first GHB dose), all GHB, including that from the second dose, will have been eliminated from the systemic circulation. GHB was also well tolerated by narcoleptic patients in this study. No adverse experience was reported.

12. Conclusions

The capacity limited elimination kinetics was observed in three out of six patients who had been administered two consecutive 3 g oral doses of GHB, 4 h apart. From a pharmacokinetic perspective, dividing the nightly GHB dose into two portions and administering the two portions to narcoleptic patients at a 2.5- to 4-h interval was rational because the elimination half-life of GHB was short (<1 h). The pharmacokinetic profiles of GHB in narcoleptic patients who had been receiving this agent nightly for years appeared to be comparable to those in alcohol dependent patients (Ferrara, 1992).

EXAMPLE 4

SODIUM OXYBATE FORMULATION STUDY

I. Study Objectives

This example described ways that sodium oxybate may be prepared and tested for stability to determine preferred formulations. Various formulations of sodium oxybate in water were prepared under different conditions of mixing and with addition of selected acidulents at multiple pH levels (Neo-Pharm Laboratories, Blainville, Quebec). Selected formulations were placed on real time and accelerated stability. Earlier studies have demonstrated that degradation products are formed in acidic conditions and that antimicrobial effectiveness is limited at high pH. Therefore several acidulents across a range of 6.0–9.0 were evaluated.

II. Study Design-Part I

The following experimental work is designed to be performed in two stages. Initial studies were conducted to evaluate the impact of conditions of formulation, pH and acidulent on the resultant levels of impurities, specified and unspecified, and potency of sodium oxybate. Sodium oxybate was prepared (MDS Neo-Pharm Laboratories, Quebec Canada), under different conditions of mixing and with addition of selected acidulents at multiple pH levels. These formulations of sodium oxybate acidulent were then tested.

A. Preliminary studies

1. Formulations description

All formulations were prepared at a concentration of 500 mg/cc of sodium oxybate in water. Three acidulents (HCl, malic acid, and phosphoric acid), were selected and tested at pH 6.0, 7.5 and 9.0.

2. Method of formulation

Solutions, were prepared using the described methods:

a. Rapid mix method

Sodium oxybate was dissolved in water and concentrated acidulent was added immediately without temperature control. Temperature of solution was monitored and recorded prior to and during addition of acidulent. The time of equiliberation to room temperature was also recorded. After the solution reached ambient room temperature, it was filtered through a 10 Mm filter.

b. Cool mix method:

Sodium oxybate was dissolved in water. Acidulent was diluted to 10% and slowly added. The solution was cooled by water with jacket or ice bath. Monitor and record the temperature of the solution was monitored and recorded during addition of acidulent. The time of equilibrium from room temperature was also recorded. The preferred maximum temperature should be maintained at less than 40° C. The solution was filtered through a 10 μm filter.

c. Reverse order of addition:

Acidulent was added to water and cooled to room temperature. The sodium oxybate was dissolved in the diluted acidulent solution. The temperature of solution was monitored and recorded during addition of sodium oxybate. The solution was filtered through a 10 μm filter.

d. Sodium oxybate control

Sodium oxybate was dissolved in water to a concentration of 500 mg/cc with no added acidulent. The final pH was recorded and the solution was filtered through a 10 μm (micron or micrometer) filter.

3. Solution data:

Data was recorded for each solution which included: 1) date of preparation 2) date of analysis, 3) amount of acidulent required to achieve target pH, 4) length of time for dissolution of sodium oxybate, 5) temperature profile of solution over time of solution preparation to be recorded at 15 minute intervals, 6) final pH of solution.

4. Testing requirements:

The following methods were used to test the prepared solutions: pH, HPLC (High Pressure Liquid Chromatography) for potency (sodium oxybate), and for impurities. Time 0 analysis was performed immediately (within 24 h). RRT=(relative retention time).

B. Summary of Part I:

1. Preliminary Evaluation of Sodium Oxybate Formulations

Tables 13, 14 and 15 provide test results for the three methods of preparation of sodium oxybate formulations.

TABLE 13

Formulation Study/PR98068
Results of Formulation Study - Time Zero determinations of Sodium Oxybate, GBL and Unspecified Impurities
Preparation Method A

| Addition of Concentrated Acidulent* (Amount of Acidulent in 1000 ml) Date of Preparation/Date of Assay [Specification] | Target pH [Target ± 0.5] | Final pH | Sodium Oxybate mg/cc % [95–105%] | Impurities Specified % GBL [≦0.5%] | Impurities Unspecified % [≦0.1% Total] |
|---|---|---|---|---|---|
| HCl (4/23/98) (10 drops over 2 minutes) | pH 9.0 | 9.0 | 509 mg/cc 101% | 0.009% | RRT 4.88 = 0.01% |
| (2.5 ml/4 minutes) | pH 7.5 | 7.5 | 507 mg/cc 101% | 0.01% | RRT 4.89 = 0.02% |
| (45 ml/34 minutes) | pH 6.0 | 6.0 | 504 mg/cc 101% | 0.033% | RRT 4.89 = 0.33% |
| Malic Acid (4/24/98) (0.12 gm) | pH 9.0 | 9.1 | 498 mg/cc 99.6% | 0.009% | RRT 4.89 = 0.01% |
| (1.6 gm) | pH 7.5 | 7.6 | 506 mg/cc 101% | 0.009% | RRT 4.89 = 0.01% |
| (25 gm) | pH 6.0 | 6.2 | 493 mg/cc 98.6% | 0.011% | RRT 4.89 = 0.01% |
| $H_3PO_4$ (4/24/98) (2 drops) | pH 9.0 | 9.0 | 493 mg/cc 98.6% | 0.009% | RRT 4.89 = 0.01% |
| (1.0 ml) | pH 7.5 | 7.5 | 493 mg/cc 98.6% | 0.009% | RRT 4.89 = 0.02% |
| (17.3 ml) | pH 6.0 | 6.1 | 497 mg/cc 99.4% | 0.063% | RRT 4.89 = 0.02% |
| Sodium Oxybate Control No Acidulent | n.a. | 9.8 | 500 mg/cc 100% | 0.009% | RRT 4.89 = 0.04% |

*Method A = Mix Method with Concentrated Acidulent and Temperature Monitoring

TABLE 14

Preparation Method B

| Addition of Diluted Acidulent* (Amount of Acidulent in 1000 ml) Date of Preparation/Date of Assay [Specification] | Target pH [Target ± 0.5] | Final pH | Sodium Oxybate mg/ml % [95–105%] | Impurities Specified % GBL [≦0.5%] | Impurities Unspecified % [≦0.1% Total] |
|---|---|---|---|---|---|
| HCl (25%) (4/28/98) (20 drops) | pH 9.0 | 9.1 | 500 mg/cc 100% | 0.009% | RRT 4.88 = 0.01% |
| (8.0 ml) | pH 7.5 | 7.6 | 499 mg/cc 99.8% | 0.009% | RRT 4.88 = 0.01% |
| (175 ml) | pH 6.0 | 6.0 | 502 mg/cc 101% | 0.016% | RRT 4.88 = 0.02% |
| $H_3PO_4$ (25%) (4/29/98) (0.3 ml) | pH 9.0 | 8.9 | 499 mg/cc 99.8% | 0.007% | RRT 4.92 = 0.02% |
| (4.0 ml) | pH 7.5 | 7.5 | 497 mg/cc 99.4% | 0.008% | RRT 4.89 = 0.02% |
| (120 ml) | pH 6.0 | 6.0 | 499 mg/cc 99.8% | 0.019% | RRT 4.89 = 0.01% |
| Malic Acid (500 mg/cc) (4/30/98) (0.115 gm/0.23 ml) | pH 9.0 | 9.0 | 495 mg/cc 99% | 0.008% | RRT 4.92 = 0.02% |
| (1.75 mg/3.5 ml) | pH 7.5 | 7.4 | 488 mg/cc 97.5% | 0.009% | RRT 4.92 = 0.01% |
| (35 gm/70 ml) | pH 6.0 | 6.0 | 487 mg/cc 97.0% | 0.013% | RRT 4.92 = 0.01% |

*Acidulent added slowly at the rate of 2–3 drops/second

TABLE 15

Preparation Method C

| Reverse Order of Addition*<br>(Amount of Acidulent in 1000 ml)<br>Date of Preparation/Date of Assay<br>[Specification] | Target pH<br>[Target ± 0.5] | Final pH | Sodium Oxybate<br>mg/ml %<br>[95–105%] | Impurities<br>Specified<br>% GBL<br>[≦0.5%] | Impurities<br>Unspecified %<br>[≦0.1% Total] |
|---|---|---|---|---|---|
| HCl (5/1/98) | pH 9.0 | 9.0 | 497 mg/cc<br>99.4% | 0.006% | RRT 4.92 = 0.03% |
| (20 drops) | | | | | |
| (2.4 ml) | pH 7.5 | 7.6 | 504 mg/cc<br>101% | 0.004% | RRT 4.92 = 0.04% |
| (45 ml) | pH 6.0 | 6.0 | 493 mg/cc<br>98.6% | 0.044% | RRT 4.92 = 0.04% |
| $H_3PO_4$ (5/4/98) | pH 9.0 | 8.9 | 496 mg/cc<br>99.2% | 0.005% | RRT 4.91 = 0.03% |
| (0.08 ml) | | | | | |
| (1.0 ml) | pH 7.5 | 7.6 | 496 mg/cc<br>99.2% | 0.004% | RRT 4.91 = 0.04% |
| (30 ml) | pH 6.0 | 6.1 | 489 mg/cc<br>97.8% | 0.023% | RRT 4.91 = 0.04% |
| Malic Acid (5/5/98) | pH 9.0 | 9.0 | 495 mg/cc<br>99% | 0.006% | RRT 4.93 = 0.02% |
| (0.12 gm) | | | | | |
| (1.6 gm) | pH 7.5 | 7.6 | 497 mg/cc<br>99.4% | 0.004% | RRT 4.93 = 0.04% |
| (35 gm) | pH 6.0 | 6.2 | 495 mg/cc<br>99% | 0.044% | RRT 4.93 = 0.04% |

*Acidulent added to water first, GHB added second.

Review of the data indicated that the optimum method for preparation of sodium oxybate with minimal impurity levels is Method B: Controlled mixing with diluted acidulent. Method 2b resulted in formulations with lowest levels of GBL.

2. Conclusions.

Additional evaluations were carried out on selected formulations: 1) sodium oxybate with HCl as acidulent, at pH 7.5, and 2) sodium oxybate with malic acid as acidulent, pH 6.0, 7.5, and 9.0.

III. Study Design-Part II

Microbial Challenge and Stability Tested to determine the most preferred embodiments, the number of formulations was limited to three based on the data prepared from the above experiments.

A. Kinetic Stability Study with Selected Formulations

Samples of formulations are stored in tightly closed containers. Storage Conditions were 25° C., 40° C., and 60° C. Time points in brackets were tested at the inventor's discretion. The samples were tested according to the following schedule: at 25° C. storage temperature, the assay points will be 0, 14, 28, 45, 60 days and 120 days; at 40° C. storage temperature, the assay points will be 0, 7, 14, 28, 45, 60 days; at 60° C. storage temperature, the assay points will be at 0, 3, 7, 14, 28, 45 days, and, 60 days.

The testing requirements included pH, HPLC for sodium oxybate (duplicate injections of single sample preparation), and impurities, specified and unspecified.

B. Preservative Effectiveness Testing of selected formulations

Microbial challenge testing of formulations was preformed according to USP XXIII, <51>, Eighth Supplement. Solutions are determined to "Pass or Fail" based upon the USP criteria for perservative effectivness which states: For Bacteria, "Not less than 1 log reduction from the initial microbial count at 14 days and no increase from the 14 days count at 28 days;" and for yeast and molds, "No increase from the initial calculated count at 14 and 28 days." Solutions which met these criteria were designated as "Pass" and those that did not meet these criteria were designated as "Fail".

C. Summary Stability Results:

1. Formulations prepared with Malic Acid as acidulents:
   a. Malic Acid, pH 6.0 formulation (25°), GBL and impurity A levels were very low on Day 0, however, by Day 45 GBL levels had reached 2.8%. Impurity A increased from 0.01 to 1.0%, and pH increased from 6.0 to 6.3 by day 45. This formulation stored at 40° C. and 60° C. showed GBL levels up to 5.4%, impurity A levels increased to 2.3%, and pH increased to 6.3 by Day 14.
   b. Malic Acid, pH 7.5 formulation (25° C.), GBL levels were 0.009% on Day 0, and increased to 0.17% by day 45. Impurity A increased from 0.01% to 0.1% and pH increased from 7.5 to 7.9. Malic acid, pH 7.5 GBL levels are reached (40° C.) and 60° C. a maximum of 0.22%. Impurity A levels reached 0.1% and pH increased to 8.0. Under accelerated conditions, all parameters reached an apparent maximum by Day 7 and did not increase significantly thereafter.
   c. Malic Acid, pH 9.0 formulation (25° C.,) GBL levels measure 0.008% on Day 0, and increased slightly to 0.013% on Day 45. Impurity A did not increase nor did pH increase. Under accelerated conditions, GBL increased from 0.008% to a maximum of 0.018% by Day 14. Impurity A increased slightly from 0.10 to 0.014% by Day 14.

2. Formulations prepared with HCl as acidulents.

HCl, pH 6.0 formulation (25°) GBL levels measured 2.8% by Day 30, and impurity A 0.004%, and pH 6.0. Accelerated storage conditions (40° C.) GBL levels were measured at 6.6%, and impurity A measured 3.1% by Day 30.

HCl, pH 7.5 formulation (25%) GBL levels measured 0 041% on Day 0, Impurity A measured 0.02%, and by Day 18 GBL measured to 0.12% and impurity A to 0.07%. Under accelerated conditions (40° C. and 60° C.), GBL increased to a maximum of 0.21%, impurity A increased from 0.02% to 0.1%, and pH increased from 7.5 to 8.0. As with Malic Acid at pH 7.5, the measured parameters reached maximum by Day 7 and did not increase significantly thereafter.

HCl, pH 9.0 formulation (25° C.) GBL levels reached 0.022% by Day 18. Impurity A stayed constant at 0.01% for 18 days. Under accelerated conditions (40° C.) GBL levels were equivalent to 25° C. storage (0.21%). Impurity A showed no increase over 25° C. conditions.

3. Conclusions.

Formulations selected for microbial challenge testing were the following: HCl, pH 7.5, and malic acid, pH 7.5. The rationale for this decision was twofold. First, the formulations were selected based on minimal formation of GBL and impurity A. Second, the formulations were selected to maintain a pH in the neutral range.

EXAMPLE 5

FURTHER EVALUATION OF SODIUM OXYBATE FORMULATIONS

Purpose: To prepare, test and evaluate multiple formulations of Sodium Oxybate and two formulations using alternative salts of garnma-hydroxybutyrate.

Scope: Various formulations of Sodium Oxybate in water were prepared with addition of selected acidulents at multiple pH levels. Solutions were prepared and tested at Neo-Pharm Laboratories, Blainville, Quebec. All formulations successfully prepared were placed on limited stability. Earlier studies have demonstrated that degradation products are formed in acidic conditions and that antimicrobial effectiveness is limited at high pH. Conditions of varying pH and concentrations of sodium oxybate previously not evaluated were prepared and tested.

Procedures: Solutions were prepared as summarized and microbial challenge testing carried out as follows:

I. Evaluation of Sodium Oxybate Formulations

Purpose: To prepare, test and evaluate multiple formulations of Sodium Oxybate and two formulations using alternative salts of gamma-hydroxybutyrate.

Scope: Various formulations of Sodium Oxybate in water were prepared with addition of selected acidulents at multiple pH levels. Selected formulations were studied for limited stability. Earlier studies demonstrated that degradation products are formed in acidic conditions and that antimicrobial effectiveness is limited at high pH. Conditions of varying pH and concentrations of sodium oxybate previously not evaluated were prepared and tested.

Responsibility: It was the responsibility of Neo-Pharm Laboratories to prepare selected formulations and perform testing per this protocol. Orphan Medical, New Medicine Development and Quality Assurance were responsible for reviewing raw data at the decision point, defining which formulations will be included in stability testing. Orphan Medical was also responsible for reviewing final results (raw data) and the final report.

Procedure: The following formulations were prepared by scientists at Neo-Pharm following the steps listed below and dispensed into containers (amber PET 240 ml bottle OMI CS-460) and closures (Clic-Loc 111, 24–400, OMI CS-470) to a volume of 200 ml each bottle. The bottles were tested by 28-day microbial challenge and by limited stability testing at 25° C. including, appearance, pH, potency, and impurity profile on day 1 (day of preparation) and day 28. Formulations Prepared and Evaluated Using Sodium Oxybate:

TABLE 16

Formulations Prepared and Evaluated Using Sodium Oxybate

| Formulation ID No. | Sodium Oxybate Concentration | Acidulent | Final pH |
|---|---|---|---|
| 1 | 500 mg/cc | Malic Acid | 7.5 |
| 2 | 250 mg/cc | Malic Acid | 7.5 |
| 3 | 350 mg/cc | Malic Acid | 7.5 |
| 4 | 450 mg/cc | Malic Acid | 7.5 |
| 5 | 550 mg/cc | Malic Acid | 7.5 |
| 6 | 650 mg/cc | Malic Acid | 7.5 |
| 7 | 500 mg/cc | Citric Acid | 7.5 |
| 8 | 500 mg/cc | Malic Acid | 5.0 |

1. Preparation: Method for preparation of various formulations: As previously determined in PR98068, the method of choice for preparation of liquid formulations of sodium oxybate was the following:

a. For a one liter quantity of product, add the sodium oxybate in 500 ml of purified and stir until dissolved. Prepare a 10% solution of the acid (Malic or Citric) and add slowly to the solution of sodium oxybate. The solution should be monitored for pH and temperature and both variables recorded at reasonable intervals (every 10 or 15 minutes). When the target pH is attained, the solution will be Q. S. to 1 liter, and pH rechecked and recorded.

b. The final solutions will be filtered through 10 µm filters and 200 mL dispensed into 5 amber PET bottles with closures (provided by Orphan Medical, Inc.). Two bottles will be used for microbial challenge studies and the remaining three bottles will be placed on limited stability.

2. Testing: Formulations were tested by two methods of evaluation:

a. Limited stability evaluation:
      (1) Storage Conditions: 25° C.
      (2) Pull Points: Day 0 (day of preparation), and day 28
      (3) Testing Requirements:

| Test | Method |
|---|---|
| Appearance | Visual |
| Potency | HPLC Neopharm 764 |
| Impurities | HPLC Neopharm 793DT |
| pH | USP <791> | b. Microbial challenge:
      (1) Storage Conditions: Microbial challenge studies of above formulations were set up with 5 microorganisms and stored for 28 days at 20–25° C., per USP<51>Eighth Supplement.
      (2) Microorganisms: After a sufficient quantity of each formulation is prepared, aliquots were inoculated with 5 microorganisms at a concentration of at least $10^5$ microorganisms/cc:
         (a) *Escherichia coli*, ATCC 8739
         (b) *Pseudomonas aeruginosa*, ATCC 9027
         (c) *Staphylococcus aureus*, ATCC 6538
         (d) *Aspergillus niger*, ATCC 18404
         (e) *Candida albicans*, ATCC 10231
      (3) Time Points: A determination of the viable cell concentration in each inoculated container was performed after 0, 1, 3, 7, 14, 21 and 28 days.

B. Formulations To Be Prepared From Alternative Salts of Gamma-Hydroxybutyrate: This work may be staged to take place at a later time than the work described above.

TABLE 17

Formulation Detail

| Formulation ID No. | Salt of GHB | Concentration of Salt of GHB | Acidultent | Final pH |
|---|---|---|---|---|
| 9 | Calcium salt | 500 mg/cc (Or maximum possible*) | Malic Acid (If compatible) | 7.5 |

1. Solubility determination: Little information is available about the solubility of this alternative salt of gamma-hydroxybutyrate and a determination of solubility was done in advance of efforts to prepare formulations for evaluation by stability and microbial challenge. Maximum solubility is evaluated for pH unadjusted soluations and within the pH range desired for this formulation (pH 6.0–8.0). If solubility is limited, the formulation will be changed to accommodate the solubility limitations. The preferred acidulent for this work is Malic acid. If acid is not compatible with the salt, then an alternative acid can be selected.

2. Preparation: Method for preparation of alternative salt formulations:

a. The previously described method (Part A) is used for preparation of formulations of calcium gamma-hydroxybutyrate at the concentrations and specified pH determined by solubility experiments.

b. The final solutions were filtered through 10 μm filters and dispensed into 5 amber PET bottles with closures (provided by Orphan Medical, Inc.). Two bottles are used for microbial challenge studies and two bottles are placed on limited stability. The remaining bottles are retained for any additional studies at a future time.

3. Testing: Formulations are tested as described above.

C. Reporting of Results: The results will be reported for the Stability and Microbial Challenge results in standard format as defined by the described Orphan Medical Development. Copies of HPLC chromatograms and any raw data from these studies will be provided with results.

D. Acceptance Criteria: Specific acceptance criteria for this study can be described analogous to those for sodium oxybate.

Results: Summarized as follows in Tables 18, 19 and 20 for various studies.

TABLE 18

Result Summary
Results of Protocol 98126 Microbial Challenge Study

|  | 0 | Day 1 | Day 7 | Day 14 | Day 21 | Day 28 |
|---|---|---|---|---|---|---|
| Lot Number MCH1064-33 | | | | | | |
| GHB, pH 7.50, 500 mg/cc Malic Acid | | | | | | |
| *E. coli* | 490,000 | 5,500 | <100 | <10 | <10 | <10 |
| *P. aeruginosa* | 141,000 | 21,600 | <100 | <10 | <10 | <10 |
| *S. aureus* | 1,035,000 | 405,000 | 79,500 | 8,300 | 1,645 | 375 |
| *C. albicans* | 835,000 | 147,000 | <100 | <10 | <10 | <10 |
| *A. niger* | 370,000 | 285,000 | 120,500 | 246,500 | 148,500 | 183,000 |
| Lot Number MCH1064-35 | | | | | | |
| GHB, pH 7.50, 250 mg/cc Malic Acid | | | | | | |
| *E. coli* | 705,000 | 229,500 | <100 | <10 | <10 | <10 |
| *P. aeruginosa* | 224,500 | 5,200 | <100 | <10 | <10 | <10 |
| *S. aureus* | 1,135,000 | 390,000 | 262,500 | 31,500 | 4,250 | 155 |
| *C. albicans* | 705,000 | 435,000 | 52,000 | 850 | <10 | <10 |
| *A. niger* | 510,000 | 515,000 | 155,500 | 176,000 | 147,500 | 184,000 |
| Lot Number MCH1064-37 | | | | | | |
| GHB, pH 7.50, 350 mg/cc Malic Acid | | | | | | |
| *E. coli* | 365,000 | 310,000 | 13,400 | <10 | <10 | <10 |
| *P. aeruginosa* | 205,000 | 15,600 | 50 | <10 | <10 | <10 |
| *S. aureus* | 1,170,500 | 605,000 | 67,500 | <60 | 60 | <10 |
| *C. albicans* | 870,000 | 355,000 | 8,300 | <10 | <10 | <10 |
| *A. niger* | 540,000 | 525,000 | 172,000 | 155,500 | 155,500 | 163,500 |
| Lot Number MCH1064-43 | | | | | | |
| GHB, pH 7.50, 550 mg/cc Malic Acid | | | | | | |
| *E. coli* | 425,000 | 63,500 | 700 | <10 | <10 | <10 |
| *P. aeruginosa* | 171,500 | 211,500 | 250 | <10 | <10 | <10 |
| *S. aureus* | 1,020,000 | 520,000 | 41,500 | 1,050 | 180 | 10 |
| *C. albicans* | 880,000 | 157,500 | 800 | <10 | <10 | <10 |
| *A. niger* | 545,000 | 505,000 | 131,000 | 156,500 | 205,000 | 187,500 |
| Lot Number MCH1064-45 | | | | | | |
| GHB, pH 7.50, 550 | | | | | | |

TABLE 18-continued

Result Summary
Results of Protocol 98126 Microbial Challenge Study

|  | 0 | Day 1 | Day 7 | Day 14 | Day 21 | Day 28 |
|---|---|---|---|---|---|---|
| mg/cc Malic Acid | | | | | | |
| E. coli | 660,000 | 58,500 | 450 | <10 | <10 | <10 |
| P. aeruginosa | 896,000 | 14,450 | 900 | <10 | <10 | <10 |
| S. aureus | 860,000 | 132,000 | 19,750 | 935 | 110 | 45 |
| C. albicans | 1,125,000 | 166,000 | <100 | <10 | <10 | <10 |
| A. niger | 530,000 | 530,000 | 105,500 | 153,000 | 157,500 | 177,000 |
| Lot Number MCH1064-47 | | | | | | |
| GHB, pH 7.50, 650 mg/cc Malic Acid | | | | | | |
| E. coli | 630,000 | 119,000 | 1,350 | <10 | <10 | <10 |
| P. aeruginosa | 183,500 | 5,900 | 50 | <10 | <10 | <10 |
| S. aureus | 890,000 | 650,000 | 76,000 | 14,550 | 510 | 1,150 |
| C. albicans | 675,000 | 145,500 | <100 | <10 | <10 | <10 |
| A. niger | 535,000 | 385,000 | 103,000 | 162,000 | 187,000 | 173,000 |
| Lot Number MCH1064-85 | | | | | | |
| Ca-Oxybate, pH 7.50, 500 mg/cc Malic Acid | | | | | | |
| E. coli | 425,000 | 121,000 | 1,650 | <10 | <10 | <10 |
| P. aeruginosa | 420,000 | 22,000 | 300 | <10 | <10 | <10 |
| S. aureus | 265,000 | 2,000 | <100 | <10 | <10 | <10 |
| C. albicans | 565,000 | 440,000 | 29,500 | <1000 | <10 | <10 |
| A. niger | 1,310,000 | 965,000 | 370,000 | 640,000 | 690,000 | 675,000 |
| Lot Number MCH1064-49 | | | | | | |
| GHB, pH 7.50, 500 mg/cc Citric Acid | | | | | | |
| E. coli | 615,000 | 6,500 | <100 | <10 | <10 | <10 |
| P. aeruginosa | 69,500 | 14,600 | <100 | <10 | <10 | <10 |
| S. aureus | 650,000 | 305,000 | 1,700 | <10 | <10 | <10 |
| C. albicans | 720,000 | 107,000 | <100 | <10 | <10 | <10 |
| A. niger | 375,000 | 380,000 | 99,500 | 178,500 | 212,500 | 165,500 |

TABLE 19

Result Summary
Data from December 30, 1997

| | (n = 3) Inoculu | 0 | Day 1 | Day 3 | Day 7 | Day 14 | Day 21 | Day 28 | Results |
|---|---|---|---|---|---|---|---|---|---|
| GHB (7.5) 750 mg/cc | | | | | | | | | |
| E. coli | 470,000 | 160,000 | 64,500 | 4,300 | 420 | <10 | <10 | <10 | |
| P. aeruginosa | 437,500 | 152,000 | 3,500 | 10 | <10 | <10 | <10 | <10 | |
| S. aureus | 447,500 | 330,000 | 24,500 | 42,000 | 8,050 | 1,935 | 15 | 10 | |
| C. albicans | 375,000 | 234,500 | 28,000 | 1,950 | <10 | <10 | 10 | <10 | |
| A. niger | 475,500 | 395,000 | 395,000 | 229,000 | 101,500 | 161,500 | 101,000 | 202,000 | |
| 750 mg/cc + 0.2% MP/PP, pH 7.50 | | | | | | | | | |
| E. coli | 470,000 | 127,000 | <1,000 | <10 | <10 | <10 | <10 | <10 | |
| P. aeruginosa | 437,500 | 61,000 | <1,000 | <10 | <10 | <10 | <10 | <10 | |
| S. aureus | 447,500 | 350,000 | 3,000 | 4,050 | <10 | <10 | <10 | <10 | |
| C. albicans | 375,000 | 103,500 | <1,000 | <10 | <10 | <10 | <10 | <10 | |
| A. niger | 457,500 | 315,000 | 415,000 | 35,500 | 79,500 | 38,500 | 87,500 | 6,400 | |
| 750 mg/cc + 0.1% MP/PP, pH 7.5 | | | | | | | | | |
| E. coli | 470,000 | 157,000 | 7,000 | <10 | <10 | <10 | <10 | <10 | |
| P. aeruginosa | 437,500 | 90,000 | <1,000 | <10 | <10 | <10 | <10 | <10 | |
| S. aureus | 447,500 | 239,000 | 5,500 | 16,950 | 600 | <10 | <10 | <10 | |
| C. albicans | 375,000 | 169,000 | <1,000 | <100 | <10 | <10 | <10 | <10 | |
| A. niger | 457,500 | 335,000 | 425,000 | 34,500 | 168,500 | 90,500 | 95,500 | 99,000 | |

TABLE 19-continued

Result Summary
Data from December 30, 1997

| | (n = 3) Inoculu | 0 | Day 1 | Day 3 | Day 7 | Day 14 | Day 21 | Day 28 | Results |
|---|---|---|---|---|---|---|---|---|---|
| 750 mg/cc + 0.2% Potassium sorbate, pH 7.5 | | | | | | | | | |
| E. coli | 470,000 | 180,000 | 735,000 | 6,200 | 475 | <10 | <10 | <10 | |
| P. aeruginosa | 437,500 | 152,000 | 1,000 | <10 | <10 | <10 | <10 | <10 | |
| S. aureus | 447,500 | 264,000 | 27,500 | 49,800 | 14,550 | 2,370 | <10 | <10 | |
| C. albicans | 375,000 | 300,000 | 41,500 | 3,800 | <10 | <10 | <10 | <100 | |
| A. niger | 457,500 | 325,000 | 360,000 | 25,000 | 202,000 | 500,000 | 345,000 | 425,000 | |
| GHB (pH 6.0) 500 mg/cc | | | | | | | | | |
| E. coli | 470,000 | 221,000 | 40,000 | 100 | <10 | <10 | <10 | <10 | |
| P. aeruginosa | 437,500 | 172,000 | 3,000 | <10 | <10 | <10 | <10 | <10 | |
| S. aureus | 447,500 | 320,000 | <1,000 | 30 | <10 | <10 | <10 | <10 | |
| C. albicans | 375,000 | 310,000 | 14,000 | 100 | <10 | <10 | <10 | <10 | |
| A. niger | 475,500 | 270,000 | 355,000 | 84,000 | 120,000 | 48,500 | 41,000 | 8,600 | |
| | | | | | | | | | PASS |
| 500 mg/cc + 0.2% MP/PP, pH 6.0 | | | | | | | | | |
| E. coli | 470,000 | 163,000 | <1,000 | <10 | <10 | <10 | <10 | <10 | |
| P. aeruginosa | 437,500 | 60,000 | <1,000 | <10 | <10 | <10 | <10 | <10 | |
| S. aureus | 447,500 | 243,000 | <1,000 | <10 | <10 | <10 | <10 | <10 | |
| C. albicans | 375,000 | 150,500 | <1,000 | <100 | <10 | <10 | <10 | <10 | |
| A. niger | 475,500 | 400,000 | 38,000 | <10 | <10 | <10 | <10 | <10 | |
| | | | | | | | | | PASS |
| 500 mg/cc + 0.1% MP/PP, pH 6.0 | | | | | | | | | |
| E. coli | 470,000 | 206,000 | <1,000 | <10 | <10 | <10 | <10 | <10 | |
| P. aeruginosa | 437,500 | 118,000 | <1,000 | <10 | <10 | <10 | <10 | <10 | |
| S. aureus | 447,500 | 330,000 | <1,000 | <10 | <10 | <10 | <10 | <10 | |
| C. albicans | 375,000 | 221,000 | <1,000 | <100 | <10 | <10 | <10 | <10 | |
| A. niger | 475,500 | 355,000 | 93,500 | 59,000 | 8,700 | 315 | 35 | <10 | |
| | | | | | | | | | PASS |
| 500 mg/cc + 0.2% Potassium sorbate, pH 6.0 | | | | | | | | | |
| E. coli | 470,000 | 222,000 | 46,500 | 150 | <10 | <10 | <10 | <10 | |
| P. aeruginosa | 437,500 | 136,000 | <1,000 | <10 | <10 | <10 | <10 | <10 | |
| S. aureus | 447,500 | 410,000 | <1,000 | 130 | <10 | <10 | <10 | <10 | |
| C. albicans | 375,000 | 395,000 | 28,500 | <100 | <10 | <10 | <10 | <10 | |
| A. niger | 475,500 | 405,000 | 270,000 | 63,000 | 51,000 | 49,500 | 39,000 | 11,150 | |
| | | | | | | | | | PASS |

TABLE 20

Result Summary

| | Inoculum | 0 | Day 1 | Day 3 | Day 7 | Day 14 | Day 21 | Day 28 |
|---|---|---|---|---|---|---|---|---|
| Data from Study Dated December 30, 1997 | | | | | | | | |
| GHB (pH 6.0) 500 mg/cc | | | | | | | | |
| E. coli | 470,000 | 221,000 | 40,000 | 100 | <10 | <10 | <10 | <10 |
| P. aeruginosa | 437,500 | 172,000 | 3,000 | <10 | <10 | <10 | <10 | <10 |
| S. aureus | 447,500 | 320,000 | <1,000 | 30 | <10 | <10 | <10 | <10 |
| C. albicans | 375,000 | 310,000 | 14,000 | 100 | <10 | <10 | <10 | <10 |
| A. niger | 475,500 | 270,000 | 355,000 | 84,000 | 120,000 | 48,500 | 41,000 | 8,600 |
| Data From Study Begun March 12, 1998 | | | | | | | | |
| GHB (pH 6.0) 500 mg/cc | | | | | | | | |
| E. coli | 500,000 | 370,000 | nd | nd | <100 | <10 | <10 | <10 |
| P. aeruginosa | 350,000 | 198,500 | nd | nd | <100 | <10 | <10 | <10 |
| S. aureus | 280,000 | 480,000 | nd | nd | <100 | <10 | <10 | <10 |
| C. albicans | 450,000 | 340,000 | nd | nd | <100 | <10 | <10 | <10 |
| A. niger | 450,000 | 445,000 | nd | nd | 9,050 | 20,500 | 9,450 | 1,120 |
| GHB (pH 6.0) | | | | | | | | |

TABLE 20-continued

Result Summary

| | Inoculum | 0 | Day 1 | Day 3 | Day 7 | Day 14 | Day 21 | Day 28 |
|---|---|---|---|---|---|---|---|---|
| 500 mg/cc | | | | | | | | |
| E. coli | 500,000 | 199,000 | nd | nd | <100 | <10 | <10 | <10 |
| P. aeruginosa | 350,000 | 192,500 | nd | nd | <100 | <10 | <10 | <10 |
| S. aureus | 280,000 | 300,000 | nd | nd | <100 | <10 | <10 | <10 |
| C. albicans | 450,000 | 370,000 | nd | nd | <100 | <10 | <10 | <10 |
| A. niger | 450,000 | 445,000 | nd | nd | 10,100 | 22,750 | 3,800 | 4,050 |
| GHB (pH 9.0) 500 mg/cc | | | | | | | | |
| E. coli | 500,000 | 320,000 | nd | nd | <100 | <10 | <10 | <10 |
| P. aeruginosa | 350,000 | 12,000 | nd | nd | <100 | <10 | <10 | <10 |
| S. aureus | 280,000 | 530,000 | nd | nd | <100 | <10 | <10 | <10 |
| C. albicans | 450,000 | 510,000 | nd | nd | <100 | <10 | <10 | <10 |
| A. niger | 450,000 | 345,000 | nd | nd | 13,800 | 158,500 | 315,000 | 110,500 |
| GHB (pH 9.0) 500 mg/cc | | | | | | | | |
| E. coli | 500,000 | 305,000 | nd | nd | <100 | <10 | <10 | <10 |
| P. aeruginosa | 350,000 | 20,000 | nd | nd | <100 | <10 | <10 | <10 |
| S. aureus | 280,000 | 495,000 | nd | nd | <100 | <10 | <10 | <10 |
| C. albicans | 450,000 | 380,000 | nd | nd | <100 | <10 | <10 | <10 |
| A. niger | 450,000 | 355,000 | nd | nd | 12,550 | 157,500 | 365,000 | 365,000 |
| GHB (pH 6.0 + Excipients) 500 mg/cc | | | | | | | | |
| E. coli | 500,000 | 96,000 | nd | nd | <100 | <10 | <10 | <10 |
| P. aeruginosa | 350,000 | 26,000 | nd | nd | <100 | <10 | <10 | <10 |
| S. aureus | 280,000 | 155,000 | nd | nd | <100 | <10 | <10 | <10 |
| C. albicans | 450,000 | 205,000 | nd | nd | <100 | <10 | <10 | <10 |
| A. niger | 450,000 | 131,500 | nd | nd | 6,250 | 1,825 | 870 | 370 |
| GHB (pH 6.0 + Excipients) 500 mg/cc | | | | | | | | |
| E. coli | 500,000 | 93,000 | nd | nd | <100 | <10 | <10 | <10 |
| P. aeruginosa | 350,000 | 30,500 | nd | nd | <100 | <10 | <10 | <10 |
| S. aureus | 280,000 | 185,000 | nd | nd | <100 | <10 | <10 | <10 |
| C. albicans | 450,000 | 135,000 | nd | nd | <100 | <10 | <10 | <10 |
| A. niger | 450,000 | 121,500 | nd | nd | 5,400 | 1,785 | 795 | 505 |

TABLE 21

Result Summary

| GHB (pH 7.50) | HCl | July 2, 1998 Start Date | | | | | | |
|---|---|---|---|---|---|---|---|---|
| 500 mg/cc | Initial Conc | 0 | Day 1 | Day 3 | Day 7 | Day 14 | Day 21 | Day 28 |
| E. coli | 97000 | 82000 | 19200 | nd | 1000 | <10 | <10 | <10 |
| P. aeruginosa | 48500 | 29500 | 520 | nd | <10 | <10 | <10 | <10 |
| S. aureus | 54500 | 58000 | 42350 | nd | 4950 | 245 | <10 | <10 |
| C. albicans | 58500 | 38500 | 1060 | nd | <100 | <10 | <10 | <10 |
| A. niger | 77500 | 48000 | 21450 | nd | 46000 | 46000 | 38000 | 54000 |
| GHB (pH 7.50) | Malic Acid | | | | | | | |
| 500 mg/cc | Initial Conc | 0 | Day 1 | Day 3 | Day 7 | Day 14 | Day 21 | Day 28 |
| E. coli | 97000 | 83000 | 44450 | nd | 3050 | 70 | <10 | <10 |
| P. aeruginosa | 48500 | 15650 | 545 | nd | <10 | <10 | <10 | <10 |
| S. aureus | 54500 | 59500 | 48400 | nd | 17400 | 6500 | 820 | 505 |
| C. albicans | 58500 | 44000 | 6200 | nd | 500 | <10 | <10 | <10 |
| A. niger | 77500 | 35500 | 24100 | nd | 28000 | 49000 | 44500 | 44000 |

For Category 1C Products:
Bacteria: Not less that 1 log reduction from the initial count at 14 days, and no increase from the 14 days count at
28 days.
Yeast and Molds: No increase from the initial calculated count at 14 and 28 days.

| GHB (pH 7.50) | HCl | July 2, 1998 Start Date | | | | | | |
|---|---|---|---|---|---|---|---|---|
| 500 mg/cc | Initial Co | 0 | Day 1 | Day 3 | Day 7 | Day 14 | Day 21 | Day 28 |

TABLE 21-continued

Result Summary

| | | | | | | | | |
|---|---|---|---|---|---|---|---|---|
| E. coli | 9.70E+04 | 8.20E+04 | 1.92E+04 | nd | 1.00E+03 | <10 | <10 | <10 |
| P. aeruginosa | 4.85E+04 | 2.95E+04 | 5.20E+02 | nd | <10 | <10 | <10 | <10 |
| S. aureus | 5.45E+04 | 5.80E+04 | 4.24E+04 | nd | 4.95E+03 | 2.45E+02 | <10 | <10 |
| C. albicans | 5.85E+04 | 3.95E+04 | 1.06E+03 | nd | <100 | <10 | <10 | <10 |
| A. niger | 7.75E+04 | 4.80E+04 | 2.15E+04 | nd | 4.60E+04 | 4.60E+04 | 3.80E+04 | 5.40E+04 |
| GHB (pH 7.50) 500 mg/cc | Malic Acid Initial Co | 0 | Day 1 | Day 3 | Day 7 | Day 14 | Day 21 | Day 28 |
| E. coli | 9.70E+04 | 8.30E+04 | 4.45E+04 | nd | 3.05E+03 | 7.00E+01 | <10 | <10 |
| P. aeruginosa | 4.85E+04 | 1.57E+04 | 5.45E+02 | nd | <10 | <10 | <10 | <10 |
| S. aureus | 5.45E+04 | 5.95E+04 | 4.84E+04 | nd | 1.74E+04 | 6.50E+03 | 8.20E+02 | 5.05E+02 |
| C. albicans | 5.85E+04 | 4.40E+04 | 6.20E+03 | nd | 5.00E+02 | <10 | <10 | <10 |
| A. niger | 7.75E+04 | 3.55E+04 | 2.41E+04 | nd | 2.80E+04 | 4.90E+04 | 4.45E+04 | 4.40E+04 |

TABLE 22 pH Variable Result Summary

| | Inoculum | 0 | Day 14 | Day 28 |
|---|---|---|---|---|
| GHB, pH 7.5 750 mg/cc 12/30/97 | | | | |
| E. coli | 470,000 | 160,000 | <10 | <10 |
| P. aeruginosa | 437,500 | 152,000 | <10 | <10 |
| S. aureus | 447,500 | 330,000 | 1,935 | 10 |
| C. albicans | 375,000 | 234,500 | <10 | <10 |
| A. niger | 475,500 | 395,000 | 161,500 | 202,000 |
| GHB, pH 7.5 750 mg/cc + 0.2% MP/PP 12/30/97 | | | | |
| E. coli | 470,000 | 127,000 | <10 | <10 |
| P. aeruginosa | 437,500 | 61,000 | <10 | <10 |
| S. aureus | 447,500 | 350,000 | <10 | <10 |
| C. albicans | 375,000 | 103,500 | <10 | <10 |
| A. niger | 457,500 | 315,000 | 38,500 | 6,400 |
| GHB, pH 7.5 750 mg/cc + 0.1% MP/PP | | | | |
| E. coli | 470,000 | 157,000 | <10 | <10 |
| P. aeruginosa | 437,500 | 90,000 | <10 | <10 |
| S. aureus | 447,500 | 239,000 | <10 | <10 |
| C. albicans | 375,000 | 169,000 | <10 | <10 |
| A. niger | 457,500 | 335,000 | 90,500 | 99,000 |
| GHB, pH 7.5 750 mg/cc + 0.2% Potassium sorbate | XXXXXX | | | |
| E. coli | | | | |
| P. aeruginosa | | | | |
| S. aureus | | | | |
| C. albicans | | | | |
| A. niger | | | | |
| GHB, pH 6.0 500 mg/cc + 0.2% Potassium sorbate 12/30/97 | | | | |
| E. coli | 470,000 | 222,000 | <10 | <10 |
| P. aeruginosa | 437,500 | 136,000 | <10 | <10 |
| S. aureus | 447,500 | 410,000 | <10 | <10 |
| C. albicans | 375,000 | 395,000 | <10 | <10 |
| A. niger | 475,500 | 405,000 | 49,500 | 11,150 |
| GHB, pH 6.0 500 mg/cc + Excipients 3/12/98 | | | | |
| E. coli | 500,000 | 93,000 | <10 | <10 |
| P. aeruginosa | 350,000 | 30,500 | <10 | <10 |
| S. aureus | 280,000 | 185,000 | <10 | <10 |
| C. albicans | 450,000 | 135,000 | <10 | <10 |
| A. niger | 450,000 | 121,500 | 1,785 | 505 |
| GHB, pH 9.0 500 mg/cc 3/12/98 | | | | |
| E. coli | 500,000 | 320,000 | <10 | <10 |
| P. aeruginosa | 350,000 | 12,000 | <10 | <10 |
| S. aureus | 280,000 | 530,000 | <10 | <10 |
| C. albicans | 450,000 | 510,000 | <10 | <10 |
| A. niger | 450,000 | 345,000 | 158,500 | 110,500 |
| GHB, pH 9.0 500 mg/cc 3/12/98 | | | | |
| E. coli | 500,000 | 305,000 | <10 | <10 |
| P. aeruginosa | 350,000 | 20,000 | <10 | <10 |
| S. aureus | 280,000 | 495,000 | <10 | <10 |
| C. albicans | 450,000 | 380,000 | <10 | <10 |
| A. niger | 450,000 | 355,000 | 157,500 | 365,000 |
| GHB, pH 6.0 500 mg/cc 12/30/97 | | | | |
| E. coli | 470,000 | 221,000 | <10 | <10 |
| P. aeruginosa | 437,500 | 172,000 | <10 | <10 |
| S. aureus | 447,500 | 320,000 | <10 | <10 |
| C. albicans | 375,000 | 310,000 | <10 | <10 |
| A. niger | 475,500 | 270,000 | 48,500 | 8,600 |
| GHB, pH 6.0 500 mg/cc + 0.2% MP/PP 12/30/97 | | | | |
| E. coli | 470,000 | 163,000 | <10 | <10 |
| P. aeruginosa | 437,500 | 60,000 | <10 | <10 |
| S. aureus | 447,500 | 243,000 | <10 | <10 |
| C. albicans | 375,000 | 150,500 | <10 | <10 |
| A. niger | 475,500 | 400,000 | <10 | <10 |
| GHB, pH 6.0 500 mg/cc + 0.1% MP/PP 12/30/97 | | | | |
| E. coli | 470,000 | 206,000 | <10 | <10 |
| P. aeruginosa | 437,500 | 118,000 | <10 | <10 |
| S. aureus | 447,500 | 330,000 | <10 | <10 |
| C. albicans | 375,000 | 221,000 | <10 | <10 |
| A. niger | 475,500 | 355,000 | 315 | <10 |
| GHB, pH 6.0 500 mg/cc 3/12/98 | | | | |
| E. coli | | | | |
| P. aeruginosa | | | | |
| S. aureus | | | | |

TABLE 22-continued pH Variable Result Summary

|  | Inoculum | 0 | Day 14 | Day 28 |
|---|---|---|---|---|
| C. albicans |  |  |  |  |
| A. niger |  |  |  |  |
| GHB, pH 6.0 |  |  |  |  |
| 500 mg/cc |  |  |  |  |
| 3/12/98 |  |  |  |  |
| E. coli | 500,000 | 199,000 | <10 | <10 |
| P. aeruginosa | 350,000 | 192,500 | <10 | <10 |
| S. aureus | 280,000 | 300,000 | <10 | <10 |
| C. albicans | 450,000 | 370,000 | <10 | <10 |
| A. niger | 450,000 | 445,000 | 22,750 | 4,050 |
| GHB, pH 6.0 |  |  |  |  |
| 500 mg/cc + Excipients |  |  |  |  |
| 3/12/98 |  |  |  |  |
| E. coli | 500,000 | 96,000 | <10 | <10 |
| P. aeruginosa | 350,000 | 26,000 | <10 | <10 |
| S. aureus | 280,000 | 155,000 | <10 | <10 |
| C. albicans | 450,000 | 205,000 | <10 | <10 |
| A. niger | 450,000 | 131,500 | 1,825 | 370 |
| GHB, pH 7.50 |  |  |  |  |
| 500 mg/cc, HCl 7/2/98 |  |  |  |  |
| E. coli | 97000 | 82000 | <10 | <10 |
| P. aeruginosa | 48500 | 29500 | <10 | <10 |
| S. aureus | 54500 | 58000 | 245 | <10 |
| C. albicans | 58500 | 38500 | <10 | <10 |
| A. niger | 77500 | 48000 | 46000 | 54,000 |
| GHB, pH 7.5 |  |  |  |  |
| 500 mg/cc, Malic Acid |  |  |  |  |
| 7/2/98 |  |  |  |  |
| E. coli | 97000 | 83000 | 70 | <10 |
| P. aeruginosa | 48500 | 15650 | <10 | <10 |
| S. aureus | 54500 | 59500 | 6500 | 505 |
| C. albicans | 58500 | 44000 | <10 | <10 |
| A. niger | 77500 | 35500 | 49000 | 44,000 |

Short term stability testing was carried out as described in Appendix A and results are summarized in—Results of Limited Stability Testing—Xyrem oral solution—are show as follows:

TABLE 23-A

| ORPHAN MEDICAL INC. | DATE: 26/01/1999 |
|---|---|
| 13911, Ridgedale Drive |  |
| Minnetonka, (MN) 55305 |  |
| USA | NO.: 333198 |
| CERTIFICATE OF ANALYSIS | |

| OXYBATE SODIUM, LIQUID FORM. | LOT: MCH1064-3 |
|---|---|
| (28 DAYS CHALLENGE TEST) | CODE: |
| PROTOCOL 98126 | REQUISITION: 1741 |
| ORPHAN MEDICAL | |

| TEST | SPECIFICATION | RESULT | PROCEDURE |
|---|---|---|---|
| Description | Clear to slightly opalescent solution. | Conforms | ORGANOLEPTIC |
| Potency | Report | d512 mg/ml (102%) | NPLC-793 |
| Impurities total | ≦2.0% | 0.068% | NPLC-793D |
| Impurities specified GBL-RRT 1.6 | Gamma-Butyrolactone (RRT = 1.6) ≦0.5% | RRT 1.45:0.021% | NPLC-793D |
|  | Impurity A (RRT 4.3) : ≦0.5% | RRT 4.17:0.02% |  |
| Impurities unspecified | Ind. imp. ≦0.1% | RRT 1.28:0.02% RRT 3.79:0.007% | NPLC-793D |
| PH | Report | 7.6 | USP <791> |

TABLE 23-A-continued

| Challenge Test | Conforms to USP (0, 1, 7, 14, 21, 28 days) | Conforms | USP 23 <51> S.8 |
|---|---|---|---|

COMMENTS:

Initial test
Formulation 1: 500 mg/cc; Malic acid; pH 7.5
THIS CERTIFICATE CORRECTS AND REPLACES CERTIFICATE 328841

TABLE 23-B

| ORPHAN MEDICAL INC. | DATE: 21/01/1999 |
|---|---|
| 13911, Ridgedale Drive |  |
| Minnetonka, (MN) 55305 |  |
| USA | NO.: 331347 |
| CERTIFICATE OF ANALYSIS | |

| OXYBATE SODIUM, LIQUID FORMULATION | LOT: MCH1064-3 CODE: |
|---|---|
| PROTOCOL 98126 | REQUISITION: 1741 |
| ORPHAN MEDICAL | |

| TEST | SPECIFICATION | RESULT | PROCEDURE |
|---|---|---|---|
| Description | Clear to slightly opalescent solution. | Conforms | ORGANOLEPTIC |
| Potency | Report | 510 mg/ml (102%) | NPLC-793-D |
| Impurities total | ≦2.0% | 0.36% | NPLC-793D |
| Impurities specified | Gamma-Butyrolactone (RRT = 1.6):≦0.5% | RRT 1.46:0.23% | NPLC-793D |
|  | Impurity A (RRT 4.3): ≦ 0.5% | RRT 4.31:0.1% |  |
| Impurities unspecified | Ind. imp. ≦0.1% | *A | NPLC-793D |
| PH | Report | 7.9 | USP <791> |

COMMENTS:

28 days (25° C., 60% RH)
Formulation 1: 500 mg/cc; Malic acid; pH 7.5
*A: RRT 1.30: 0.02%
RRT 3.93 : 0.008%

TABLE 23-C

| ORPHAN MEDICAL INC. | DATE: 26/01/1999 |
|---|---|
| 13911, Ridgedale Drive |  |
| Minnetonka, (MN) 55305 |  |
| USA | NO.: 333197 |
| CERTIFICATE OF ANALYSIS | |

| OXYBATE SODIUM, LIQUID FORM. | LOT: MCH1064-3 |
|---|---|
| (28 DAYS CHALLENGE TEST) | CODE: |
| PROTOCOL 98126 | REQUISITION: 1741 |
| ORPHAN MEDICAL | |

| TEST | SPECIFICATION | RESULT | PROCEDURE |
|---|---|---|---|
| Description | Clear to slightly opalescent solution. | Conforms | ORGANOLEPTIC |
| Potency | Report | 258 mg/ml (103%) | NPLC-793-D |
| Impurities total | ≦2.0% | 0.045% | NPLC-793D |
| Impurities specified GBL-RRT 1.6 | Gamma-Butyrolactone (RRT=1.6): ≦0.5% |  |  |

TABLE 23-C-continued

| | | | |
|---|---|---|---|
| | Impurity A (RRT 4.3) : ≦0.5% | RRT 4.17:0.02% | |
| Impurities unspecified | Ind. imp. ≦0.1% | RRT 3.79:0.009% | NPLC-793D |
| PH | Report | 7.6 | USP <791> |

TABLE 23-C-continued

| | | | |
|---|---|---|---|
| Challenge test | Conforms to USP (0, 1, 7, 14, 21, 28 days) | Conforms | USP 23 <51> S.8 |

COMMENTS:

Initial test
Formulation 2: 250 mg/cc; Malic acid; pH 7.5
THIS CERTIFICATE CORRECTS AND REPLACES CERTIFICATE 328845

TABLE 23-D

ORPHAN MEDICAL INC.     DATE: 21/01/1999
13911, Ridgedale Drive
Minnetonka, (MN) 55305
USA     NO.: 331346
CERTIFICATE OF ANALYSIS OXYBATE SODIUM, LIQUID     LOT: MCH1064-3
FORMULATION     CODE:
PROTOCOL 98126     REQUISITION: 1741
ORPHAN MEDICAL

| TEST | SPECIFICATION | RESULT | PROCEDURE |
|---|---|---|---|
| Description | Clear to slightly opalescent solution. | Conforms | ORGANOLEPTIC |
| Potency | Report | 256 mg/ml (102%) | NPLC-793-D |
| Impurities total | ≦2.0% | 0.18% | NPLC-793D |
| Impurities specified | Gamma-Butyrolactone (RRT = 1.6): ≦0.5% | RRT 1.46: 0.13% | NPLC-793D |
| | Impurity A (RRT 4.3): ≦0.5% | RRT 4.31: 0.03% | |
| Impurities unspecified | Ind. imp. <0.1% | *A | NPLC-793D |
| PH | Report | 7.9 | USP <791> |

COMMENTS:

28 DAYS (25° C., 60% RH)
Formulation 2: 250 mg/cc; Malic acid; pH 7.5
*A:    RRT 1.29: 0.007%
       RRT 3.93: 0.008%

TABLE 23-E

ORPHAN MEDICAL INC.     DATE: 26/01/1999
13911, Ridgedale Drive
Minnetonka, (MN) 55305
USA     NO.: 333196
CERTIFICATE OF ANALYSIS OXYBATE SODIUM, LIQUID FORM.     LOT: MCH1064-3
(28 DAYS CHALLENGE TEST)     CODE:
PROTOCOL 98126     REQUISITION: 1741
ORPHAN MEDICAL

| TEST | SPECIFICATION | RESULT | PROCEDURE |
|---|---|---|---|
| Description | Clear to slightly opalescent solution. | Conforms | ORGANOLEPTIC |
| Potency | Report | 360 mg/ml (103%) | NPLC-793 |
| Impurities total | <2.0% | 0.050% | NPLC-793D |
| Impurities specified GBL-RRT 1.6 | Gamma-Butyrolactone (RRT = 1.6): <0.5% | RRT 1.45: 0.017% | NPLC-793D |
| | Impurity A (RRT 4.3): <0.5% | RRT 4.17: 0.02% | |
| Impurities unspecified | Ind. imp. <0.1% | RRT 1.28: 0.006% RRT 3.79: 0.007% | NPLC-793D |
| PH | Report | 7.7 | USP <791> |

TABLE 23-E-continued

| | | | |
|---|---|---|---|
| Challenge test | Conforms to USP (0,1,7,14,21,28 days) | Conforms | USP 23 <51> S.8 |

COMMENTS:

Initial test
Formulation 3: 350 mg/cc; Malic acid; pH 7.5
THIS CERTIFICATE CORRECTS AND REPLACES CERTIFICATE 328847

TABLE 23-F

ORPHAN MEDICAL INC.  DATE: 21/01/1999
13911, Ridgedale Drive
Minnetonka, (MN) 55305
USA  NO.: 331345
CERTIFICATE OF ANALYSIS OXYBATE SODIUM, LIQUID  LOT: MCH1064-3
FORMULATION  CODE:
PROTOCOL 98126  REQUISITION: 1741
ORPHAN MEDICAL

| TEST | SPECIFICATION | RESULTAT/RESULT | PROCEDURE |
|---|---|---|---|
| Description | Clear to slightly opalescent solution. | Conforms | ORGANOLEPTIC |
| Potency | Report | 363 mg/ml (104%) | NPLC-793-D |
| Impurities total | ≦2.0% | 0.21% | NPLC-793D |
| Impurities specified | Gamma-Butyrolactone (RRT = 1.6): ≦0.5% | RRT 1.46: 0.14% | NPLC-793D |
| | Impurity A (RRT 4.3): ≦0.5% | RRT 4.31: 0.05% | |
| Impurities unspecified | Ind. imp. <0.1% | *A | NPLC-793D |
| PH | Report | 8.0 | USP <791> |

COMMENTS:

28 DAYS (25° C., 60% RH)
Formulation 3: 350 mg/cc; Malic acid; pH 7.5
*A:   RRT 1.29: 0.009%
      RRT 3.93: 0.008%

TABLE 23-G

ORPHAN MEDICAL INC.  DATE: 26/01/1999
13911, Ridgedale Drive
Minnetonka, (MN) 55305
USA  NO.: 333195
CERTIFICATE OF ANALYSIS OXYBATE SODIUM, LIQUID FORM.  LOT: MCH1064-4
(28 DAYS CHALLENGE TEST)  CODE: 1741
PROTOCOL 98126  REQUISITION: 1741
ORPHAN MEDICAL

| TEST | SPECIFICATION | RESULT | PROCEDURE |
|---|---|---|---|
| Description | Clear to slightly opalescent solution. | Conforms | ORGANOLEPTIC |
| Potency | Report | 461 mg/ml (102%) | NPLC-793 |
| Impurities total | <2.0% | 0.065% | NPLC-793D |
| Impurities specified GBL-RRT 1.6 | Gamma-Butyrolactone (RRT = 1.6): <0.5% | RRT 1.45: 0.018% | NPLC-793D |
| | Impurity A (RRT 4.3): <0.5% | RRT 4.17: 0.02% | |
| Impurities unspecified | Ind. imp. <0.1% | RRT 1.28: 0.006% RRT 3.79: 0.007% | NPLC-793D |
| PH | Report | 7.5 | USP <791> |
| Challenge test | Conforms to USP (0,1,7,14,21,28 days) | Conforms | USP 23 <51> S.8 |

TABLE 23-G-continued

COMMENTS:

Initial test

Formulation 4: 450 mg/cc; Malic acid; pH 7.5

THIS CERTIFICATE CORRECTS AND REPLACES CERTIFICATE 328875

TABLE 23-H

ORPHAN MEDICAL INC.  
13911, Ridgedale Drive  
Minnetonka, (MN) 55305  
USA

DATE: 21/01/1999

NO.: 331343

CERTIFICATE OF ANALYSIS

OXYBATE SODIUM, LIQUID FORMULATION  
PROTOCOL 98126  
ORPHAN MEDICAL

LOT: MCH1064-4  
CODE:  
REQUISITION: 1741

| TEST | SPECIFICATION | RESULT | PROCEDURE |
|---|---|---|---|
| Description | Clear to slightly opalescent solution. | Conforms | ORGANOLEPTIC |
| Potency | Report | 454 mg/ml (101%) | NPLC-793-D |
| Impurities total | $\leq 2.0\%$ | 0.40% | NPLC-793D |
| Impurities specified | Gamma-Butyrolactone (RRT = 1.6): $\leq 0.5\%$ | RRT 1.46: 0.26% | NPLC-793D |
|  | Impurity A (RRT 4.3): $\leq 0.5\%$ | RRT 4.31: 0.1% |  |
| Impurities unspecified | Ind. imp. <0.1% | *A | NPLC-793D |
| PH | Report | 7.8 | USP <791> |

COMMENTS:

28 DAYS (25° C., 60% RH)  
Formulation 4: 450 mg/cc; Malic acid; pH 7.5  
*A:   RRT 1.30: 0.03%  
       RRT 3.93: 0.008%

TABLE 23-I

ORPHAN MEDICAL INC.  
13911, Ridgedale Drive  
Minnetonka, (MN) 55305  
USA

DATE: 26/01/1999

NO.: 333194

CERTIFICATE OF ANALYSIS

OXYBATE SODIUM, LIQUID FORM.  
(28 DAYS CHALLENGE TEST)  
PROTOCOL 98126  
ORPHAN MEDICAL

LOT: MCH1064-4  
CODE:  
REQUISITION: 1741

| TEST | SPECIFICATION | RESULT | PROCEDURE |
|---|---|---|---|
| Description | Clear to slightly opalescent solution. | Conforms | ORGANOLEPTIC |
| Potency | Report | 563 mg/ml (102%) | NPLC-793 |
| Impurities total | <2.0% | 0.077% | NPLC-793D |
| Impurities specified GBL-RRT 1.6 | Gamma-Butyrolactone (RRT = 1.6): <0.5% | RRT 1.45: 0.020% | NPLC-793D |
|  | Impurity A (RRT 4.3): <0.5% | RRT 4.17: 0.02% |  |
| Impurities unspecified | Ind. imp. <0.1% | RRT 1.29: 0.03%<br>RRT 3.79: 0.007% | NPLC-793D |
| PH | Report | 7.6 | USP <791> |
| Challenge test | Conforms to USP (0,1,7,14,21,28 days) | Conforms | USP 23 <51> S.8 |

TABLE 23-I-continued

COMMENTS:

Initial test

Formulation 5: 550 mg/cc; Malic acid; pH 7.5

THIS CERTIFICATE CORRECTS AND REPLACES CERTIFICATE 328883

TABLE 23-J

ORPHAN MEDICAL INC.  
13911, Ridgedale Drive  
Minnetonka, (MN) 55305  
USA

DATE: 21/01/1999

NO.: 331341

CERTIFICATE OF ANALYSIS

OXYBATE SODIUM, LIQUID FORMULATION  
PROTOCOL 98126  
ORPHAN MEDICAL

LOT: MCH1064-4  
CODE:  
REQUISITION: 1741

| TEST | SPECIFICATION | RESULT | PROCEDURE |
|---|---|---|---|
| Description | Clear to slightly opalescent solution. | Conforms | ORGANOLEPTIC |
| Potency | Report | 561 mg/ml (102%) | NPLC-793-D |
| Impurities total | ≦2.0% | 0.56% | NPLC-793D |
| Impurities specified | Gamma-Butyrolactone (RRT = 1.6): ≦0.5% | RRT 1.46: 0.31% | NPLC-793D |
|  | Impurity A (RRT 4.3): ≦0.5% | RRT 4.31: 0.2% |  |
| Impurities unspecified | Ind. imp. <0.1% | *A | NPLC-793D |
| PH | Report | 7.9 | USP <791> |

COMMENTS:

28 DAYS (25° C., 60% RH)  
Formulation 2: 250 mg/cc; Malic acid; pH 7.5  
*A:  RRT 1.30: 0.04%  
     RRT 3.93: 0.007%

TABLE 23-K

ORPHAN MEDICAL INC.  
13911, Ridgedale Drive  
Minnetonka, (MN) 55305  
USA

DATE: 26/01/1999

NO.: 333193

CERTIFICATE OF ANALYSIS

OXYBATE SODIUM, LIQUID FORM.  
(28 DAYS CHALLENGE TEST)  
PROTOCOL 98126  
ORPHAN MEDICAL

LOT: MCH1064-4  
CODE:  
REQUISITION: 1741

| TEST | SPECIFICATION | RESULT | PROCEDURE |
|---|---|---|---|
| Description | Clear to slightly opalescent solution. | Conforms | ORGANOLEPTIC |
| Potency | Report | 666 mg/ml (102%) | NPLC-793 |
| Impurities total | <2.0% | 0.10% | NPLC-793D |
| Impurities specified GBL-RRT 1.6 | Gamma-Butyrolactone (RRT = 1.6): <0.5% | RRT 1.45: 0.025% | NPLC-793D |
|  | Impurity A (RRT 4.3): <0.5% | RRT 4.17: 0.02% |  |
| Impurities unspecified | Ind. imp. <0.1% | RRT 1.28: 0.05% RRT 3.79: 0.007% | NPLC-793D |
| PH | Report | 7.6 | USP <791> |
| Challenge test | Conforms to USP (0,1,7,14,21,28 days) | Conforms | USP 23 <51> S.8 |

TABLE 23-K-continued

COMMENTS:

Initial test

Formulation 6: 650 mg/cc; Malic acid; pH 7.5

THIS CERTIFICATE CORRECTS AND REPLACES CERTIFICATE 328885

TABLE 23-L

ORPHAN MEDICAL INC.  
13911, Ridgedale Drive  
Minnetonka, (MN) 55305  
USA

DATE: 21/01/1999

NO.: 331336

CERTIFICATE OF ANALYSIS

OXYBATE SODIUM, LIQUID  
FORMULATION  
PROTOCOL 98126  
ORPHAN MEDICAL

LOT: MCH1064-4  
CODE:  
REQUISITION: 1741

| TEST | SPECIFICATION | RESULT | PROCEDURE |
|---|---|---|---|
| Description | Clear to slightly opalescent solution. | Conforms | ORGANOLEPTIC |
| Potency | Report | 660 mg/ml (102%) | NPLC-764 |
| Impurities total | ≦2.0% | 0.81% | NPLC-793D |
| Impurities specified | Gamma-Butyrolactone (RRT = 1.6): ≦0.5% | RRT 1.46: 0.43% | NPLC-793D |
|  | Impurity A (RRT 4.3): ≦0.5% | RRT 4.31: 0.3% |  |
| Impurities unspecified | Ind. imp. <0.1% | *A | NPLC-793D |
| PH | Report | 7.8 | USP <791> |

COMMENTS:

28 DAYS (25° C., 60% RH)  
Formulation 6: 650 mg/cc; Malic acid; pH 7.5  
*A:   RRT 1.30: 0.07%  
      RRT 3.93: 0.007%

TABLE 23-M

ORPHAN MEDICAL INC.  
13911, Ridgedale Drive  
Minnetonka, (MN) 55305  
USA

DATE: 26/01/1999

NO.: 333192

CERTIFICATE OF ANALYSIS

OXYBATE SODIUM, LIQUID FORM.  
(28 DAYS CHALLENGE TEST)  
PROTOCOL 98126  
ORPHAN MEDICAL

LOT: MCH1064-4  
CODE:  
REQUISITION: 1741

| TEST | SPECIFICATION | RESULT | PROCEDURE |
|---|---|---|---|
| Description | Clear to slightly opalescent solution. | Conforms | ORGANOLEPTIC |
| Potency | Report | 518 mg/ml (104%) | NPLC-793 |
| Impurities total | <2.0% | 0.065% | NPLC-793D |
| Impurities specified GBL-RRT 1.6 | Gamma-Butyrolactone (RRT = 1.6): <0.5% | RRT 1.45: 0.018% | NPLC-793D |
|  | Impurity A (RRT 4.3): <0.5% | RRT 4.17: 0.02% |  |
| Impurities unspecified | Ind. imp. <0.1% | RRT 3.79: 0.007% RRT 5.99: 0.02% | NPLC-793D |
| PH | Report | 7.5 | USP <791> |
| Challenge test | Conforms to USP (0,1,7,14,21,28 days) | Conforms | USP 23 <51> S.8 |

TABLE 23-M-continued

COMMENTS:

Initial test
Formulation 7: 500 mg/cc; Citric acid; pH 7.5
THIS CERTIFICATE CORRECTS AND REPLACES CERTIFICATE 329033

TABLE 23-N

ORPHAN MEDICAL INC.  DATE: 21/01/1999
13911, Ridgedale Drive
Minnetonka, (MN) 55305
USA  NO.: 331335

CERTIFICATE OF ANALYSIS

OXYBATE SODIUM, LIQUID  LOT: MCH1064-4
FORMULATION  CODE:
PROTOCOL 98126  REQUISITION: 1741
ORPHAN MEDICAL

| TEST | SPECIFICATION | RESULT | PROCEDURE |
|---|---|---|---|
| Description | Clear to slightly opalescent solution. | Conforms | ORGANOLEPTIC |
| Potency | Report | 515 mg/ml (103%) | NPLC-793-D |
| Impurities total | ≦2.0% | 0.38% | NPLC-793D |
| Impurities specified | Gamma-Butyrolactone (RRT = 1.6): ≦0.5% | RRT 1.46: 0.27% | NPLC-793D |
|  | Impurity A (RRT 4.3): ≦0.5% | RRT 4.31: 0.1% |  |
| Impurities unspecified | Ind. imp. <0.1% | RRT 3.93: 0.007% | NPLC-793D |
| PH | Report | 7.9 | USP <791> |

COMMENTS:

28 DAYS (25° C., 60% RH)
Formulation 7: 500 mg/cc; Citric acid; pH 7.5

TABLE 23-O

ORPHAN MEDICAL INC.  DATE: 09/01/1999
13911, Ridgedale Drive
Minnetonka, (MN) 55305
USA  NO.: 330721

CERTIFICATE OF ANALYSIS

OXYBATE CALCIUM LIQUID FORM.  LOT: MCH1064-85
(28 DAYS CHALLENGE TEST)  CODE:
PROTOCOL 98126  REQUISITION: 1741
ORPHAN MEDICAL

| TEST | SPECIFICATION | RESULT | PROCEDURE |
|---|---|---|---|
| Description | Clear to slightly opalescent solution. | Conforms | ORGANOLEPTIC |
| Challenge Test | Conforms to USP (0,1,7,14,21 and 28 days) | Conforms | USP 23 <51> S.8 |
| Potency | Report | 501 mg/ml (100%) | NPLC-793 |
| Impurities total | <2.0% | 1.2% | NPLC-793D |
| Impurities unspecified | Ind. imp. <0.1% | *A | NPLC-793D |
| Impurities specified | Gamma-Butyrolactone Report: | RRT 1.46: 0.013% | NPLC-793D |
| PH | Report | 7.3 | USP <791> |
| Solubility study | Report | *B | PR 98126 IIA |

COMMENTS:

Initial test
500 mg/ml cc; Malic acid; pH 7.5
*A: RRT 1.31: 0.02%  RRT 1.67: 0.008%
   RRT 1.91: Interference with peak of dilution solvent cannot calculate.
   RRT 3.47: 0.1%  RRT 3.79: 0.009%  RRT 3.84: 0.01%
   RRT 4.18: 0.06%  RRT 5.10: 0.008%  RRT 5.35: 0.02%

TABLE 23-O-continued

RRT 6.74: 0.9%  RRT 6.90: 0.08%  RRT 7.41: 0.006%
*B: Maximum solubility: 700 mg/ml no pH adjustment.

TABLE 23-P

| ORPHAN MEDICAL INC. | | | DATE: 26/02/1999 |
|---|---|---|---|
| 13911, Ridgedale Drive | | | |
| Minnetonka, (MN) 55305 | | | |
| USA | | | NO.: 331307 |
| | CERTIFICATE OF ANALYSIS | | |
| OXYBATE CALCIUM LIQUID FORM. | | | LOT: MCH1064-85 |
| PROTOCOL 98126 | | | CODE: |
| ORPHAN MEDICAL | | | REQUISITION: 1741 |
| TEST | SPECIFICATION | RESULT | PROCEDURE |
| Description | Clear to slightly opalescent solution. | Conforms | ORGANOLEPTIC |
| Potency | Report | 508 mg/ml (102%) | NPLC-793 |
| Impurities total | <2.0% | 0.70% | NPLC-793D |
| Impurities unspecified | Ind. imp. <0.1% | *A | NPLC-793D |
| Impurities specified | Gamma-Butyrolactone Report: | RRT 1.37: 0.054% | NPLC-793D |
| PH | Report | 7.6 | USP <791> |

COMMENTS:

28 DAYS (25° C., 60% RH)
500 mg/ml cc; Malic acid; pH 7.5
*A:  RRT 1.17: 0.03%  RRT 3.47: 0.2%
     RRT 5.46: 0.01%  RRT 6.87: 0.3%
     RRT 7.04: 0.007%
     RRT 1.78: Can not calculate because it interfere with a dilution solvant peak.

II. Summary of Results
A. Preparation of various formulations of Sodium Oxybate and formulations using an alternative salt of GHB.

1. Various formulations of sodium oxybate were prepared as directed in the above Protocol. Sodium oxybate, 500 mg/cc with Malic Acid was not soluble at pH 5.0, and further evaluation of this solution was discontinued. All other solutions were successfully prepared as described.

2. The preparation of an alternative salt of gamma-hydroxybutyrate was described as the calcium salt, prepared at 500 mg/cc (or maximum possible) with Malic Acid at pH 7.5.

a. The calcium salt of gamma-hydroxybutyrate was prepared by Toronto Research and shipped to NeoPharm for determination of solubility and evaluation according to the Protocol. The absolute limit of solubility, without p14 adjustment, was determined to be 700 mg/cc. The pH of this solution was 8.4. Solutions of lower pH were more difficult to prepare at 500 mg/cc using Malic acid as acidulant. When pH was adjusted to 6.0 with Malic acid, the solubility of the calcium oxybate was limited (longer stirring required to solubilize). The desired solution of 500 mg/cc, pH 7.5 was prepared with Malic acid as acidulant without difficulty. Appearance of the final solution was slightly yellow in color. Copies of the laboratory record for preparation of these solutions is available.

B. Microbial Challenge Testing of the various formulations prepared by MDS NeoPharm.

The microbial challenge testing was carried as specified in the Protocol and the following table summarizes the results of microbial challenge testing of various formulations of sodium oxybate and the single calcium oxybate formulation prepared.

TABLE 24

Testing of Sodium and Calcium GHB Salts

| | pH of Solution | Microbial Challenge Result |
|---|---|---|
| Sodium Oxybate Concentration | | |
| 1. 500 mg/cc | 7.5 (Malic acid) | Pass |
| 2. 250 mg/cc | 7.5 (Malic acid) | Pass |
| 3. 350 mg/cc | 7.5 (Malic acid) | Pass |
| 4. 450 mg/cc | 7.5 (Malic acid) | Pass |
| 5. 550 mg/cc | 7.5 (Malic acid) | Pass |
| 6. 650 mg/cc | 7.5 (Malic acid) | Pass |
| 7. 500 mg/cc | 7.5 (Citric acid) | Pass |
| Calcium Oxybate Conctration | | |
| 500 mg/cc | 7.5 | Pass |

C. Short term stability evaluation of various formulations of sodium oxybate and a formulation of calcium oxybate.

Solutions were tested on day zero (preparation day) and day 28 according to the described Protocol. The results of the stability evaluation are summarized in Table 25 below:

TABLE 25

Sodium and Calcium GHB Evaluation

| Sodium oxybate solution | Potency mg/cc (%) | Impurities (Total) | Impurities (Unspecified) | Impurities (Specified-GLB) | pH |
|---|---|---|---|---|---|
| 500 mg/cc pH 7.5 Malic Acid Day 0 | 512 mg/cc (102%) | 0.68% | 0.041% | 0.027% | 7.6 |
| Day 28 | 510 mg/cc (103%) | 0.36% | 0.33% | 0.028% | 7.9 |
| 250 mg/cc pH 7.5 Malic Acid Day 0 | 258 mg/cc (103%) | 0.045% | 0.009% | 0.026% | 7.6 |
| Day 28 | 256 mg/cc (102%) | 0.18% | 0.015% | 0.16% | 7.9 |
| 350 mg/cc pH 7.5 Malic Acid Day 0 | 360 mg/cc (103%) | 0.050% | 0.013% | 0.037% | 7.7 |
| Day 28 | 363 mg/cc (104%) | 0.21% | 0.017% | 0.19% | 8.0 |
| 450 mg/cc pH 7.5 Malic Acid Day 0 | 461 mg/cc (102%) | 0.065% | 0.027% | 0.038% | 7.5 |
| Day 28 | 454 mg/cc (101%) | 0.40% | 0.038% | 0.36% | 7.8 |
| 550 mg/cc pH 7.5 Malic Acid Day 0 | 563 mg/cc (102%) | 0.077% | 0.037% | 0.040% | 7.6 |
| Day 28 | 561 mg/cc (102%) | 0.56% | 0.047% | 0.51% | 7.9 |
| 650 mg/cc pH 7.5 Malic Acid Day 0 | 666 mg/cc (102%) | 0.10% | 0.057% | 0.045% | 7.6 |
| Day 28 | 660 mg/cc (102%) | 0.81% | 0.077% | 0.73% | 7.8 |
| 500 mg/cc pH 7.5 Citric Acid Day 0 | 518 mg/cc (104%) | 0.065% | 0.027% | 0.038% | 7.5 |
| Day 28 | 515 mg/cc (103%) | 0.38% | 0.007% | 0.37% | 7.9 |

| Calcium oxybate solution | Potency | Impurities (Total) | Impurities (Specified) | Impurities (Unspecified) | pH |
|---|---|---|---|---|---|
| 500 mg/cc pH 7.5 Malic Acid Day 0 | 501 mg/cc (100%) | 1.2% | >0.1% (See C of A Attached) | 0.013% | 7.3 |
| Day 28 | 508 mg/cc (102%) | 0.70% | >0.1% (See C of A) | 0.054% | 7.6 |

D. Summary of Pertinent Solubility and Microbial Challenge Data are shown in Tables 26 and 27.

TABLE 26

Limits of Solubility

| | pH of Solution | Comments |
|---|---|---|
| Sodium oxybate Maximum Solubility | | |
| 450 mg/cc | pH 4 (HCl) | 25° |
| 500 mg/cc | pH 5 (HCl) | 25° |
| 600 mg/cc | pH 6 (HCl) | 25° |
| 750 mg/cc | pH 6.8 (HCl) | 25° |
| 750 mg/cc + | pH 10.3 | 25° |
| 1000 mg/cc Calcium oxybate Maximum Solubility | pH (unadjusted) | 65° Soluble, 25° Gel |
| 700 mg/cc | pH 8.4 (unadjusted) | 25° |
| 500 mg/cc | pH 6.0 | 25° |

TABLE 27

Microbial Challenge Results

| | pH of Solution | Microbial Challenge Result |
|---|---|---|
| Sodium oxybate Concentration (Date) | | |
| 750 mg/cc (Dec. '97) | 7.5 (HCl) | pass |
| 500 mg/cc (Dec. '97) | 6.0 (HCl) | pass |
| 500 mg/cc + Excipients (Xylitol) (March '98) | 6.0 (Malic Acid) | pass |
| 500 mg/cc (March '98) | 9.0 (HCl) | pass (Borderline aspergillus) |
| 150 mg/cc (BDL 1995) | 5.0 (HCl) | fail (aspergillus only) |
| 150 mg/cc (BDL 1995) | 7.0 (HCl) | fail (aspergillus and staph) |
| 150 mg/cc (BDL 1995) | 3.0 (HCl) | fail (aspergillus only) |
| 150 mg/cc (BDL 1995) | 10.3 (unadjusted) | fail (aspergillus and staph) |
| 500 mg/cc (May '98) | 6.0 (Malic Acid) | discontinued |
| 500 mg/cc (May '98) | 7.5 (Malic Acid) | pass |
| 500 mg/cc (May '98) | 9.0 (Malic Acid) | discontinued |
| 500 mg/cc (May '98) | 7.5 (HCl) | pass |
| 500 mg/cc | 7.5 (Malic Acid) | pass |
| 250 mg/cc | 7.5 (Malic Acid) | pass |
| 350 mg/cc | 7.5 (Malic Acid) | pass |
| 450 mg/cc | 7.5 (Malic Acid) | pass |
| 550 mg/cc | 7.5 (Malic Acid) | pass |
| 650 mg/cc | 7.5 (Malic Acid) | pass |
| 500 mg/cc | 7.5 (Citric Acid) | pass |
| Calcium oxybate Concentration (Date) | | |
| 500 mg/cc | 7.5 (Malic Acid) | pass |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,380,937
U.S. Pat. No. 4,393,236

German Patent DD 237.309 Al Brant et al., "Preparation of storage-stable sodium gamma. -hydroxybutyrate"

British Pat. No. 922,029

Aden and Stock, "Increases in brain dopamine," 1973.

Arena and Fung, "Absorption of soidum γ-hydroxybutyrate and its prodrug γ-butyrolactone: relationship between n vitro transport and in vivo absorption," J. Pharmaceutical Sciences, 69(3):356–358, 1980.

Bedard, Montplaisir, Godbout, Lapierre, "Nocturnal γ-Hydroxybutyrate—Effect on Periodic Leg Movements and Sleep Organization of Narcoleptic Patients," 12(l) :29–36, 1989.

Berthier, Bonneau, Desbordes, Chevrel, Oriot, Jaeken, Liaborit, "Possible involvement of a gamma-hydroxybutyric acid receptor in startle disease," Acta Paediatr., 83:678–80, 1994.

Broughton and Mamelak, "The treatment of narcolepsy-cataplexy with noctural gamma-hydroxybutyrate," Le Journal Canadien Des Sciences Neurologiques, 6(1):1–6, 1979.

Ferrara, Zotti, Tedeschi, Frison, Castagna, Gallimberti, Gessa, "Pharmacokinetics of γ-hydroxybutyric acid in alcohol dependent patients after single and repeated oral doses," Br. J. Clin. Pharmacol., 34:231–235, 1992.

Gallimberti, Canton, Tentile, Ferri, Cibin, Ferrara, Fadda, Gessa, "Gamma-hydroxybutyric acid for treatment of alcohol withdrawal syndrome," Clinical Pharmacology, 787–789, 1989;

Gallimberti, Ferri, Ferrara, Fadda, Gessa "Gamma-Hydroxybutyric acid in the treatment of alcohol dependence: a double-blind study," Alcohol Clin. Exp. Res., 16(4):673–676, 1992;

Gallimberti et al., "Gamma-Hydroxybutric Acid in the Treatment of Alcohol Dependence: A Double-Blind Study" Clin. Exp. Res., 16, 673–676, 1992.

Gessa and Gallimberti, "Gamma-hydroxybutyric acid in the treatment of alcohol dependent," Clin. Neuropharm., 15(1, PtA):303A–304A, 1992.

Gessa, Diana, Fadda, Colombo, "Gamma-hydroxybutyric acid (GHHHB) for treatment of ethanol dependence," Clin. Neuropharm.—Supplement, 1992.

Gessa et al., Clin. Neuropharm., 15(supp.):303A–304A, 1992.

Gessa et al., Internat. Clin. Psychopharm., 1994

Grove-White and Kelman, "Critical Flicker Frequency after small doses of Methohexitone, Diazepam and Sodium 4-Hydroxybutyrate, Brit. J Anaesth., p. 43, 110, 1971.

Grove-White and Kelman, "Effect of Methohexitone, Diazepam and Sodium 4-Hydroxybutyrate on Short-Term Memory," Brit. J. Anaesth., p. 43, 113, 1971.

Hasenbos and Gielen, "Anaesthesia for bullectomy," Anaesthesia, 40:977–980, 1985.

Hoes, Vree, Guelen, "Gamma-hydroxybutyric acid (*) as hypnotic," L'Encephale, 4(1):93–99, 1980.

Laborit, "Gamma-Hydroxybutyrate, Succinic Semialdehyde and Sleep," Laboratoire d' Eutonologie, Hôpital Boucicaut, Paris 15, France, 1973.

Ladinsky, Consolo, Zatta, Vezzani, "Mode of Action of Gamma-Butyrolactone on the Central Cholinergic System, Naunyn-Schmiedeberg's Arch. Pharmacol., 322:42–48, 1983.

Ladinsky et al., "Increases in brain acetylcholine," 1983.

Lammers, Arends, Declerck, Ferrari, Schouwink, Troost, "Gammahydroxybutyrate and Narcolepsy: A Double-Blind Placebo-Controlled Study," Sleep, 16(3)):216–220, 1993.

Lammers et al., "Gammahydroxybutyrate and narcolepsy: a double-blind placebo-controlled study," Sleep, 16(3) :216–220, 1993.

Lapierre, Montplaisir, Lamarre, Bedard, "The Effect of Gamma- Hydroxybutyrate on Nocturnal and Diurnal Sleep of Normal Subjects: Further Considerations on REM Sleep-Triggering Mechanisms," Sleep, 13(1) :24–30, 1990.

Lapierre et al., "Increases in delta sleep," 1988.

Lapierre et al., "Increases in delta sleep," 1990.

Lee, "Evidence for the β-Oxidation of Orally Administered 4-Hydroxybutyrate in Humans," Biochemical Medicine, 17, 284–291 1977.

Lee, C. R. "Evidence for the β-Oxidation of Orally Administered 4-Hydroxybutyrate in Humans" Biochem. Medicine 17, 284–291, 1977.

Lettieri and Fung, "Improved pharmacological activity via pro-drug modification: comparative pharmacokinetics of sodium γ-hydroxybutyrate and γ-butyrolactone," Research Communications in Chemical Pathology and Pharmacology, 22(1):107–118, 1978.

Mamelak, 1977; "Effects Of Gamma Hydroxybutyrate On Sleep," Biol. Psychiatry 12, 273–288.

Mamelak, "Gamma-hydroxybutyrate (GHB): An endogenous regulator of energy metabolism," Neuroscience and Biobehav. Reviews, 13:189–198, 1989.

Mamelak, "Gammahydroxybutyrate: An Endogenous Regulator of Energy Metabolism," Neuro. & Biobehav. Rev., 13 187–198, 1989.

Mamelak, 1979;

Mamelak, Escriu, Stokan "The effects of gamma-hydroxybutyrate on sleep," Biol. Psychiatry, 12(2) :273–288, 1977.

Mamelak, Escriu, Stokan, "Sleep-Inducing Effects of Gammahydroxybutyrate," The Lancet, p. 328–329, 1973.

Nema, et al., "Excipients and their use in injectable products," PDA J Pharm. Sci. Technol., 51(4):166–171, 1997.

Nema et al., "Excipients and their use in injectable products," PDA J Pharm Sci Technol., 51(4):166–171, 1997.

Palatini, Tedeschi, Frison, Padrini, Zordan, Orlando, Gallimberti, Gessa, Ferrara, "Dose dependent absorption and elimination of gamrna-hydroxybutyric acid in healthy volunteers," Eur. J. Clin. Pharmacol., 45:353–356, 1993.

Roth and Giarman, "γ-Butyrolactone and γ-Hydroxybutyric Acid-I, Distribution and Metabolism," Biochemical Pharmacology, 15:1333–1348, 1966.

Scharf, Brown, Woods, Brown, Hirschowitz, "The effects and effectiveness of gammahydroxybutyrate in patients with narcolepsy," J. Clin. Psychiatry, 46(6):222–225, 1985.

Scrima, Hartman, Johnson, Miller, "Gamma-Hydroxybutyrate Effects on Cataplexy and Sleep Attacks in Narcoleptics," Abstract, p. 134.

Scrima, Hartman, Johnson, Thomas, Hiller, "Efficacy of gamma-hydroxybutyrate versus placebo in treating narcolepsy-cataplexy: Double-blind subjective measured," Biol. Psychiatry, 26:331–343, 1989.

Scrima, Hartman, Johnson, Thomas, Hiller, "The Effects of γ-Hydroxybutyrate on the Sleep of Narcolepsy Patients: A Double-Blind Study," Sleep, 13(6):479–490, 1990.

Scrima, Hartman, Johnson, Thomas, Hiller, "The effects of gamma-hydroxybutyrate on the sleep of narcolepsy patients: A double blind study," Sleep Res., 13:479–490, 1990.

Scrima, Hartman, Johnson, Thomas, Miller, "Effects of Gamnma-Hydroxybutyrate (GHB) on Narcolepsy-Cataplexy Symptoms and MSLT Results in Male and Female Patients," Abstract, p. 251.

Scrima, Hoddes, Johnson, Cardin, Thomas, Miller, "Effect of High Altitude on a Patient with Obstructive Sleep Apnea," Abstract, p.427.

Scrima, Hoddes, Johnson, Miller, "Effect of Gamma-Hydroxybutyrate on a Patient with Obstructive Sleep Apnea," Abstract, p. 137.

Scrima, et al, "Sleep Res. 16, 134,1987, Abstract.

Sériés, Sériés, Cormier, "Effects of Enhancing Slow-Wave Sleep by Gamma-Hydroxybutyrate on Obstructive Sleep Apnea," *Am. Rev. Respir. Dis.*, 1378–1383, 1992.

Snead and Morley, "Ontogeny of gamma-hydroxybutyric acid. Regional concentration in developing rat, monkey and human brain," *Brain Res.*, 227:579–589, 1981.

Sneed, Anticonvulsants, alcohol abuse and opiate withdrawal, 1988

Stock, Magnusson, Anden, "Increase in Brain Dopamine after Axotomy or Treatment with Gammahydroxybutyric Acid due to Elimination of the Nerve Impulse Flow," *Naunyn-Schmiedeberg's Arch. Pharmacol.*, 278, 347–361, 1973.

Strong, "γ-Hydroxybutyric acid and Intracranial Pressure," *The Lancet*, Vol. I:No. 8389, 1984.

van den Bogert, Vree, van der Kleijn, Damsma, "Placentatransfer of 4-Hydroxybutyric Acid in Man."

Vickers, "Gammahydroxybutyric Acid," *Int. Anesth. Clinic*, 7:75–89, 1969.

Vickers, *Int. Anesth. Clinic* 7:75–89, 1969;

Lee, *Biochem. Med.* 17:234–291, 1977.

Yamada, Yamamoto, Fujiki, Hishikawa, Kaneko, "Effect of Butyrolactone and Gamma-Hydroxybutyrate on the EEG and Sleep Cycle in Man," *Electroenceph. Clin. Neurophysiol.*, 22:558–562, 1967.

Yamada et al., 1967.

What is claimed is:

1. A method of rendering an aqueous medium resistant to microbial growth, comprising adding the gamma-hydroxybutyrate salt to the aqueous medium, adjusting the concentration of the gamma-hydroxybutyrate salt in the aqueous medium to a final concentration of at least about 250 mg/ml, and adjusting the pH of the medium to a final pH of about 6 to about 10, so that the medium is chemically stable and resistant to microbial growth.

2. The method of claim 1 wherein the salt is sodium gamma-hydroxybutyrate.

3. The method of claim 1 or 2 wherein the final concentration is from about 310 to about 750 mg/ml and the final pH is about 6 to about 9.

4. The method of claim 1, 2, or 3 wherein the medium does not contain a preservative.

5. The method of claim 1, wherein the concentration of said gamma-hydroxybutyrate is from about 250 to about 750 mg/ml.

6. The method of claim 1, wherein said pH-adjusting agent is an organic acid.

7. The method of claim 6, wherein said acid is selected from the group consisting of malic acid, citric acid, acetic acid, boric acid, lactic acid, hydrochloric acid, phosphoric acid, sulfuric acid, sulfonic acid and nitric acid.

* * * * *

UNITED STATES PATENT AND TRADEMARK OFFICE
CERTIFICATE OF CORRECTION

| | | |
|---|---|---|
| PATENT NO. | : 6,472,431 B2 | Page 1 of 1 |
| APPLICATION NO. | : 09/470570 | |
| DATED | : October 29, 2002 | |
| INVENTOR(S) | : Harry Cook et al. | |

It is certified that error appears in the above-identified patent and that said Letters Patent is hereby corrected as shown below:

In column 70, lines 18-19, in Claim 4, delete "4. The method of claim 1, 2, or 3 wherein the medium does not contain a preservative." and
insert -- 4. The method of claim 1 or 2 wherein the medium does not contain a preservative. --, therefor.

Signed and Sealed this
Sixteenth Day of August, 2011

David J. Kappos
*Director of the United States Patent and Trademark Office*